United States Patent [19]
Caro et al.

[11] Patent Number: 5,833,618
[45] Date of Patent: *Nov. 10, 1998

[54] APPARATUS AND METHOD FOR MEASURING AN INDUCED PERTURBATION TO DETERMINE A PHYSIOLOGICAL PARAMETER

[75] Inventors: Richard G. Caro; Mark H. Sher, both of San Francisco, Calif.

[73] Assignee: Vital Insite, Inc., South San Francisco, Calif.

[ * ] Notice: The term of this patent shall not extend beyond the expiration date of Pat. No. 5,590,649.

[21] Appl. No.: 561,923

[22] Filed: Nov. 22, 1995

Related U.S. Application Data

[63] Continuation-in-part of Ser. No. 228,213, Apr. 15, 1994.

[60] Provisional application No. 60/005,179, Oct. 3, 1995.

[51] Int. Cl.$^6$ ........................................................ A61B 5/00
[52] U.S. Cl. ........................ 600/485; 600/500; 600/504; 600/561; 600/300; 600/480; 600/431
[58] Field of Search ................................ 128/630.2, 623, 128/664.7, 672–656, 713, 716, 719, 721, 2, 736, 740

[56] References Cited

U.S. PATENT DOCUMENTS 3,090,377  5/1963  Salisbury et al. .
3,095,872  7/1963  Tolles .

(List continued on next page.)

FOREIGN PATENT DOCUMENTS 0 443 267 A1  8/1991  European Pat. Off. .
WO 86/04801  8/1986  WIPO .
WO90/00029   1/1990  WIPO .

OTHER PUBLICATIONS

"Characteristics of Impact and Pulse Wave Propagation in Brachial and Radial Arteries", Milton Landowne, vol. 12, Jan. 1958, pp. 91–97.

"Dispersion and Attenuation of Small Artificial Pressure Waves in the Canine Aorta", Max Anliker, Ph.D., Michael B. Histand, M.S., and Eric Ogden, MRCS, LRCP, Circulation Research, vol. XXIII, Oct. 1968, pp. 539–551.

(List continued on next page.)

*Primary Examiner*—Robert L. Nasser
*Attorney, Agent, or Firm*—Flehr Hohbach Test Albritton & Herbert LLP

[57] ABSTRACT

A monitor for determining a patient's physiological parameter includes a calibration device configured to provide a calibration signal representative of the patient's physiological parameter. An exciter is positioned over a blood vessel of the patient for inducing a transmitted exciter waveform into the patient. A noninvasive sensor is positioned over the blood vessel, where the noninvasive sensor is configured to sense a hemoparameter and to generate a noninvasive sensor signal representative of the hemoparameter containing a component of a physiological parameter waveform and a component of a received exciter waveform. In this context, a hemoparameter is defined as any physiological parameter related to vessel blood such as pressure, flow, volume, velocity, blood vessel wall motion, blood vessel wall position and other related parameters. A processor is configured to determine a relationship between a property of the received exciter waveform and a property of the physiological parameter. The processor is connected to receive the calibration signal and the noninvasive sensor signal, and the processor is configured to process the calibration signal and the noninvasive sensor signal to determine the physiological parameter. In the preferred embodiment, the physiological parameter measured is blood pressure, however, the present invention can also be used to analyze and track other physiological parameters such as vascular wall compliance, strength of ventricular contractions, vascular resistance, fluid volume, cardiac output, myocardial contractility and other related parameters.

44 Claims, 13 Drawing Sheets

U.S. PATENT DOCUMENTS

| | | | |
|---|---|---|---|
| 3,885,551 | 5/1975 | Massie . | |
| 4,646,754 | 3/1987 | Seale | 128/677 |
| 4,718,426 | 1/1988 | Russell . | |
| 4,771,792 | 9/1988 | Seale . | |
| 4,869,261 | 9/1989 | Penaz . | |
| 4,873,987 | 10/1989 | Djordjevich et al. . | |
| 4,907,596 | 3/1990 | Schmid et al. | 128/672 |
| 5,111,817 | 5/1992 | Clark et al. . | |
| 5,148,807 | 9/1992 | Hsu . | |
| 5,237,997 | 8/1993 | Greubel et al. | 128/672 |
| 5,241,963 | 9/1993 | Shankar | 128/694 |
| 5,241,964 | 9/1993 | McQuilkin | 128/672 |
| 5,267,565 | 12/1993 | Beard | 128/687 |
| 5,279,303 | 1/1994 | Kawamura et al. | 128/683 |

OTHER PUBLICATIONS

"Measurement of Pulse–Wave Velocity Using a Beat–Sampling Technique", J.D. Pruett, J.D. Bourland, L.A. Geddes, Annals of Biomedical Engineering, vol. 16, pp. 341–347, 1988.

"Application Note #3 About Lock–In Amplifiers", Stanford Research Systems, Scientific and Engineering Instruments, 1992–1993, pp. 129–139.

"Vibration technique for indirect measurement of diastolic arterial pressure in human fingers", H. Shimazu, H. Ito, A. Kawarada, H. Kobayashi, A. Hiraiwa, K. Yamakoshi, Med. & Biol. Eng. & Comput., Mar. 1989, 27, pp. 130–136.

"Continuous Non–Invasive Blood Pressure Measurement Using Arterial Pressure Wave Velocity", R.G. Pearl, L.C. Siegel, T. Nishimura, M.H. Sher, B.T. Flaherty, J. McLoughlin, R.C. Caro, STanford University School of Medicine, 1995.

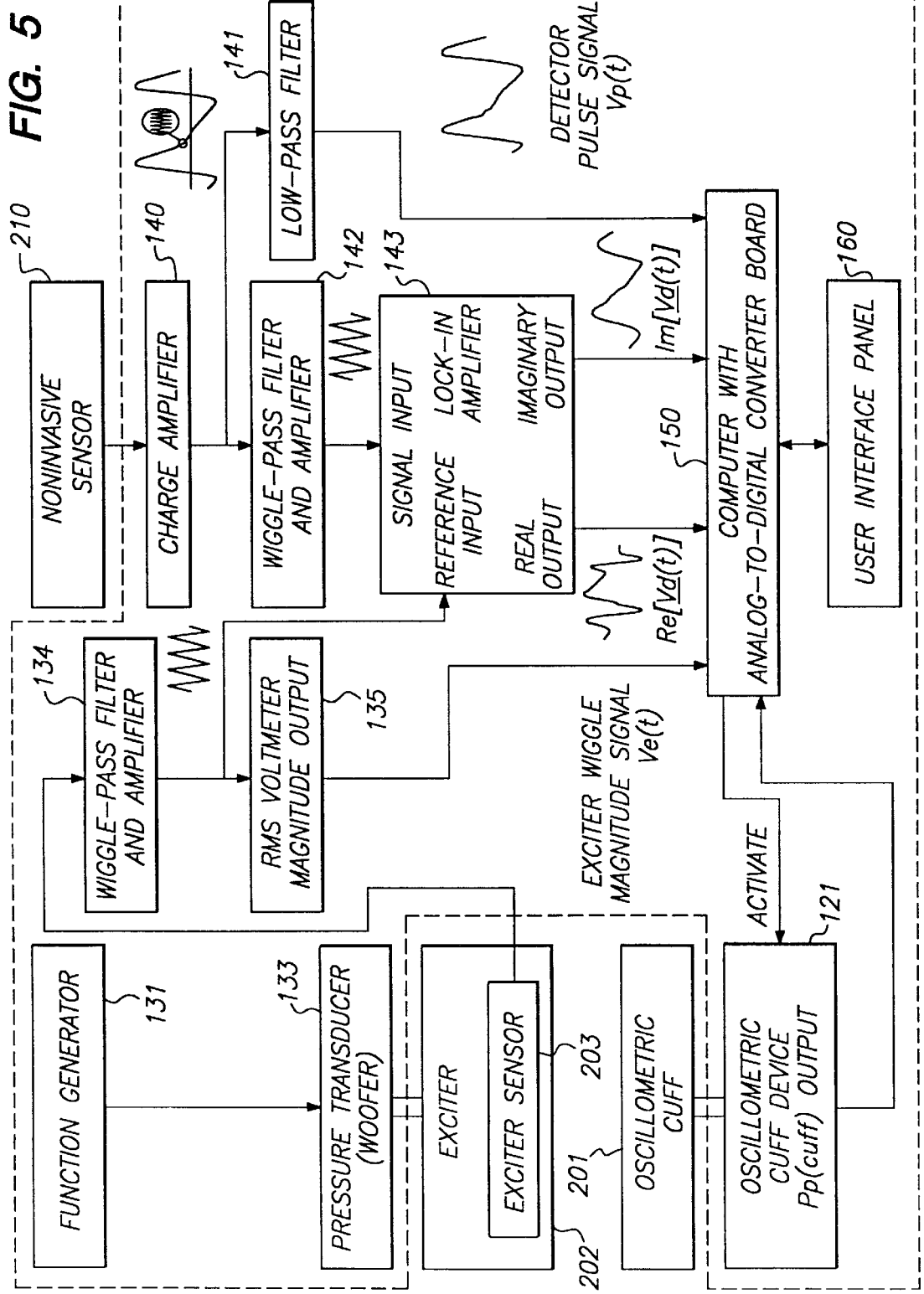

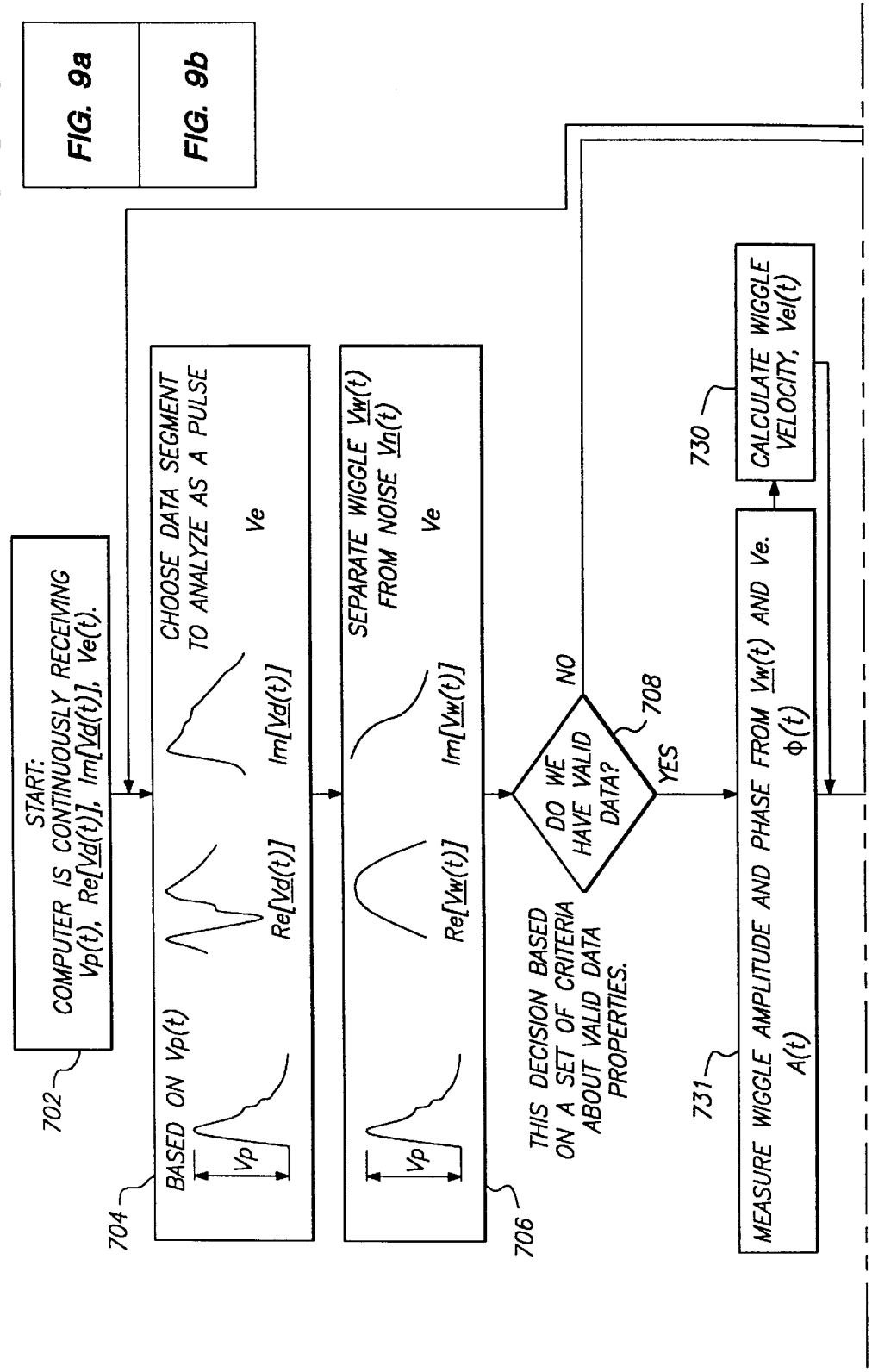

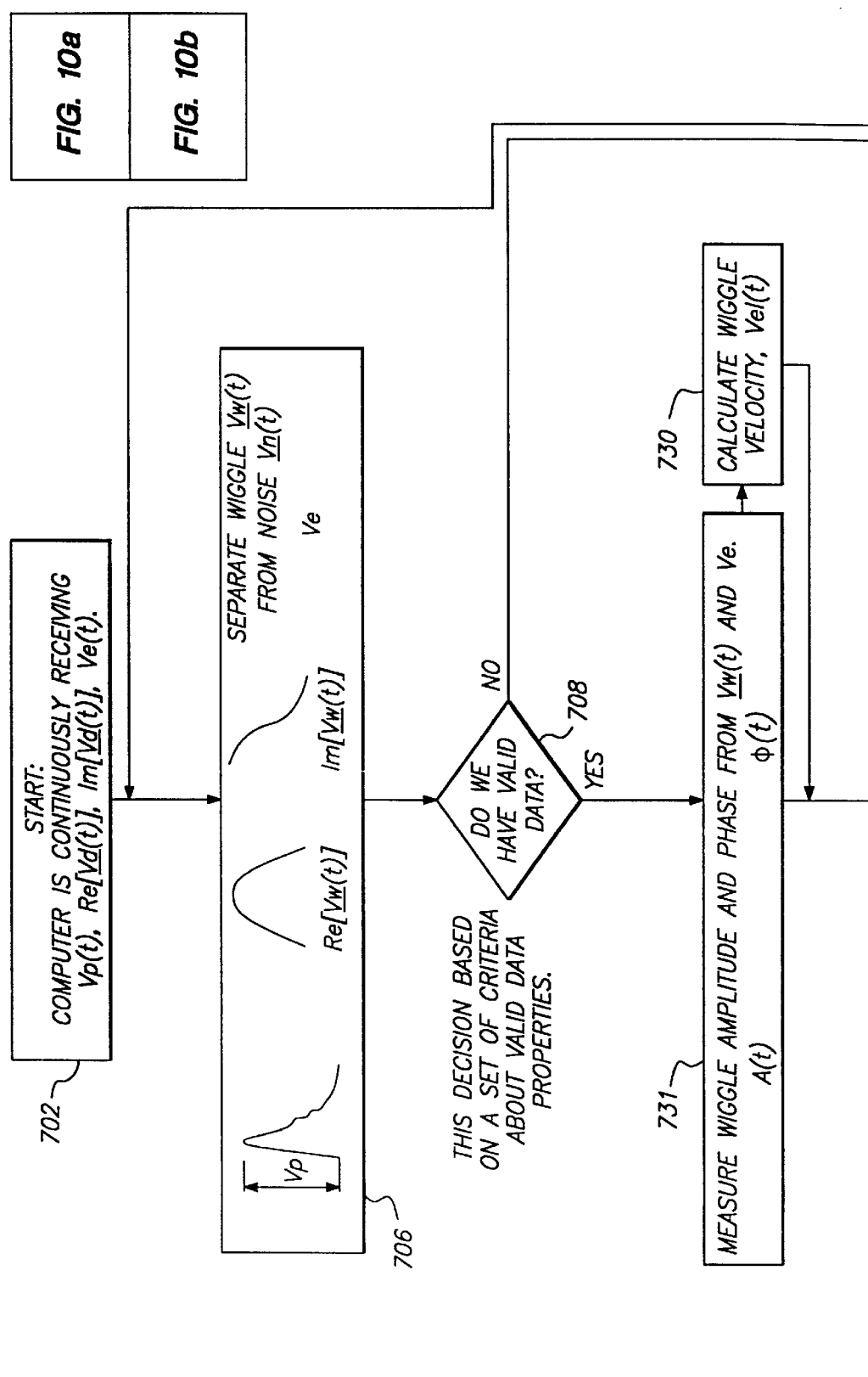

APPARATUS AND METHOD FOR MEASURING AN INDUCED PERTURBATION TO DETERMINE A PHYSIOLOGICAL PARAMETER

RELATED APPLICATIONS

This application is a continuation in part of the following patent applications and incorporates these applications by reference:

Caro, U.S. Ser. No. 08/228,213 filed on Apr. 15, 1994; and

Caro, Apparatus and Method for Measuring an Induced Perturbation to Determine a Physiological Parameter, U.S. Provisional patent application Ser. No. 60/005,179 filed on Oct. 3, 1995 (Atty Docket No. A-59155-1).

FIELD OF THE INVENTION

The present invention relates to an apparatus and method for noninvasively providing a determination of a patient's physiological parameter and other clinically important parameters.

BACKGROUND OF THE INVENTION

Blood pressure is the force within the arterial system of an individual that ensures the flow of blood and delivery of oxygen and nutrients to the tissue. Prolonged reduction or loss of pressure severely limits the amount of tissue perfusion and could therefore result in damage to or even death of the tissue. Although some tissues can tolerate hypoperfusion for long periods of time, the brain, heart and kidneys are very sensitive to a reduction in blood flow. Thus, during and after surgery, blood pressure is a frequently monitored vital sign. Blood pressure is affected, during and after surgery, by the type of surgery and physiological factors such as the body's reaction to the surgery. Moreover, blood pressure is manipulated and controlled, during and after surgery, using various medications. Often, these physiological factors and the given medications can result in a situation of rapidly changing blood pressure requiring immediate blood pressure measurement, and corrective action.

Because of changes in the patient's blood pressure, constant monitoring is important. The traditional method of measuring blood pressure is with a stethoscope, occlusive cuff and pressure manometer. However, this technique is slow, subjective in nature, requires the intervention of a skilled clinician and does not provide timely readings frequently required in critical situations.

For these reasons, two methods of measuring blood pressure have been developed: noninvasive, intermittent methods that use an automated cuff device such as an oscillometric cuff; and invasive, continuous (beat-to-beat) measurements that use a catheter.

The oscillometric cuff method typically requires 15 to 45 seconds to obtain a measurement, and should allow sufficient time for venous recovery. Thus, at best there is typically ½ to 1 minute between updated pressure measurements. This is an inordinately long amount of time to wait for an updated pressure reading when fast acting medications are administered. Also, too frequent cuff inflations over extended periods may result in ecehymosis and/or nerve damage in the area underlying the cuff. The invasive method has inherent disadvantages including risk of embolization, infection, bleeding and vessel wall damage.

To address the need for continuous, noninvasive blood pressure measurement, several systems were developed. One approach relies on blood pressure values in a patient's finger as indicative of the patient's central blood pressure, as in the cases of Penaz, U.S. Pat. No. 4,869,261 and H. Shimazu, *Vibration Techniques for Indirect Measurement of Diastolic Arterial Pressure in Human Fingers,* Med. and Biol. Eng. and Comp., vol. 27, no. 2, p. 130 (March 1989). Another system uses two cuffs, one on each arm, to determine calibration readings and continuous readings respectively. Another system transforms a time sampled blood pressure waveform into the frequency domain and determines blood pressure based on deviations of the fundamental frequency. Kaspari, et al. U.S. patent application Ser. No. 08/177,448, filed Jan. 5, 1994 provides examples of these systems. An additional class of devices, represented by L. Djordjevich et al. WO 90/00029 (PCT Application), uses electrical conductance to determine blood pressure.

A related area of interest was explored by perturbing the body tissue of patients. One class of experiments causes perturbations by inducing kinetic energy into the patient, specifically, by oscillating a blood vessel. In the work of Seale, U.S. Pat. No. 4,646,754, an attempt is described to measure blood pressure by sensing the input impedance of a blood vessel exposed to a low frequency vibration. In work by H. Hsu, U.S. Pat. No. 5,148,807, vibrations are used in a non-contact optical tonometer. Several experiments measured the velocity of excited perturbations in the blood and demonstrated a correlation between perturbation velocity and blood pressure. Such a correlation has also been demonstrated between pressure and the velocity of the natural pulse wave. However, while these studies discuss the relationship between velocity and pressure they do not propose a practical method of measuring induced perturbations to determine blood pressure. Examples of such studies are M. Landowne, *Characteristics of Impact and Pulse Wave Propagation in Brachial and Radial Arteries,* J. Appl. Physiol., vol. 12, p. 91 (1958); J. Pruett, *Measurement of Pulse-Wave Velocity Using a Beat-Sampling Technique,* Annals of Biomedical Engineering, vol. 16, p. 341 (1988); and M. Anliker, *Dispersion and Attenuation of Small Artificial Pressure Waves in the Canine Aorta,* Circulation Research, vol. 23, p.539 (October 1968).

Known techniques for measuring propagation of pressure perturbations in arteries include Tolles, U.S. Pat. No. 3,095,872 and Salisbury, U.S. Pat. No. 3,090,377. Tolles employs two sensors to detect a perturbation waveform and generate two sensor signals. The two sensor signals are compared in a phase detector. The phase difference of the sensor signals is displayed giving a signal that is capable of detecting changes in blood pressure, but which does not provide a calibrated blood pressure output. Salisbury similarly employs a sensor to detect a perturbation waveform and generate a single sensor signal. The sensor signal is compared against a reference signal. Based on the phase difference of the sensor signal, a universal formula is employed to determine the patient's blood pressure. Since it has been shown, for example by Landowne, that the relationship between pressure and signal propagation varies considerably from patient to patient, Salisbury's technique, based on a single formula, is not generally applicable.

OBJECTS AND SUMMARY OF THE INVENTION

The present invention describes an apparatus and method for measuring the induced perturbation of a patient's body tissue to determine the patient's blood pressure and other clinically important parameters.

An object of the present invention is to continuously determine a patient's blood pressure via a noninvasive sensor attached to the patient.

A related object is to induce a perturbation into a patient's blood or blood vessel and to noninvasively measure the perturbation to determine the patient's blood pressure.

A related object is to filter the noninvasive sensor signal into components including a natural component, an induced component and a noise component, and to determine the patient's blood pressure from the induced component.

A further related object is to determine a relationship between a property of an induced perturbation and a property of a physiological parameter.

A monitor for determining a patient's physiological parameter includes a calibration device configured to provide a calibration signal representative of the patient's physiological parameter. An exciter is positioned over a blood vessel of the patient for inducing a transmitted exciter waveform into the patient. A noninvasive sensor is positioned over the blood vessel, where the noninvasive sensor is configured to sense a hemoparameter and to generate a noninvasive sensor signal representative of the hemoparameter containing a component of a physiological parameter waveform and a component of a received exciter waveform. In this context, a hemoparameter is defined as any physiological parameter related to vessel blood such as pressure, flow, volume, velocity, blood vessel wall motion, blood vessel wall position and other related parameters. A processor is configured to determine a relationship between a property of the received exciter waveform and a property of the physiological parameter. The processor is connected to receive the calibration signal and the noninvasive sensor signal, and the processor is configured to process the calibration signal and the noninvasive sensor signal to determine the physiological parameter. In the preferred embodiment, the physiological parameter measured is blood pressure, however, the present invention can also be used to analyze and track other physiological parameters such as vascular wall compliance, strength of ventricular contractions, vascular resistance, fluid volume, cardiac output, myocardial contractility and other related parameters.

BRIEF DESCRIPTION OF THE FIGURES

Additions advantages of the invention will become apparent upon reading the following detailed description and upon reference to the drawings, in which:

FIG. 5 depicts a schematic diagram of the present invention;

Glossary $P_D$ diastolic blood pressure
$P_{D0}$ diastolic blood pressure at calibration
$P_S$ systolic blood pressure
$P_p$ pulse pressure
$P_w$ exciter waveform pressure
$V_d$ received exciter waveform
$V_w$ signal exciter waveform
$V_n$ noise waveform
$V_e$ exciter sensor signal (transmitted exciter waveform)
$V_P$ detected pulsatile voltage
$\Phi w$ exciter signal phase
$\Phi w_D$ exciter signal phase at diastole
Vel(t) exciter signal velocity
$Vel_D$ exciter signal velocity at diastole
$Vel_D$ exciter signal velocity at systole

DETAILED DESCRIPTION OF THE PREFERRED EMBODIMENTS

A preferred embodiment concentrates on the physiological parameter of blood pressure, however, many additional physiological parameters can be measured with the present invention including vascular wall compliance, ventricular contractions, vascular resistance, fluid volume, cardiac output, myocardial contractility and other related parameters. Those skilled in the art will appreciate that various changes and modifications can be made to the preferred embodiment while remaining within the scope of the present invention. As used herein, the term continuous means that the physiological parameter of interest is determined over a period of time, such as during the course of surgery. The implementation of portions of the invention in a digital computer is performed by sampling various input signals and performing the described procedures on a set of samples. Hence, a periodic determination of the physiological parameter of interest is within the definition of the term continuous.

Figure 1:
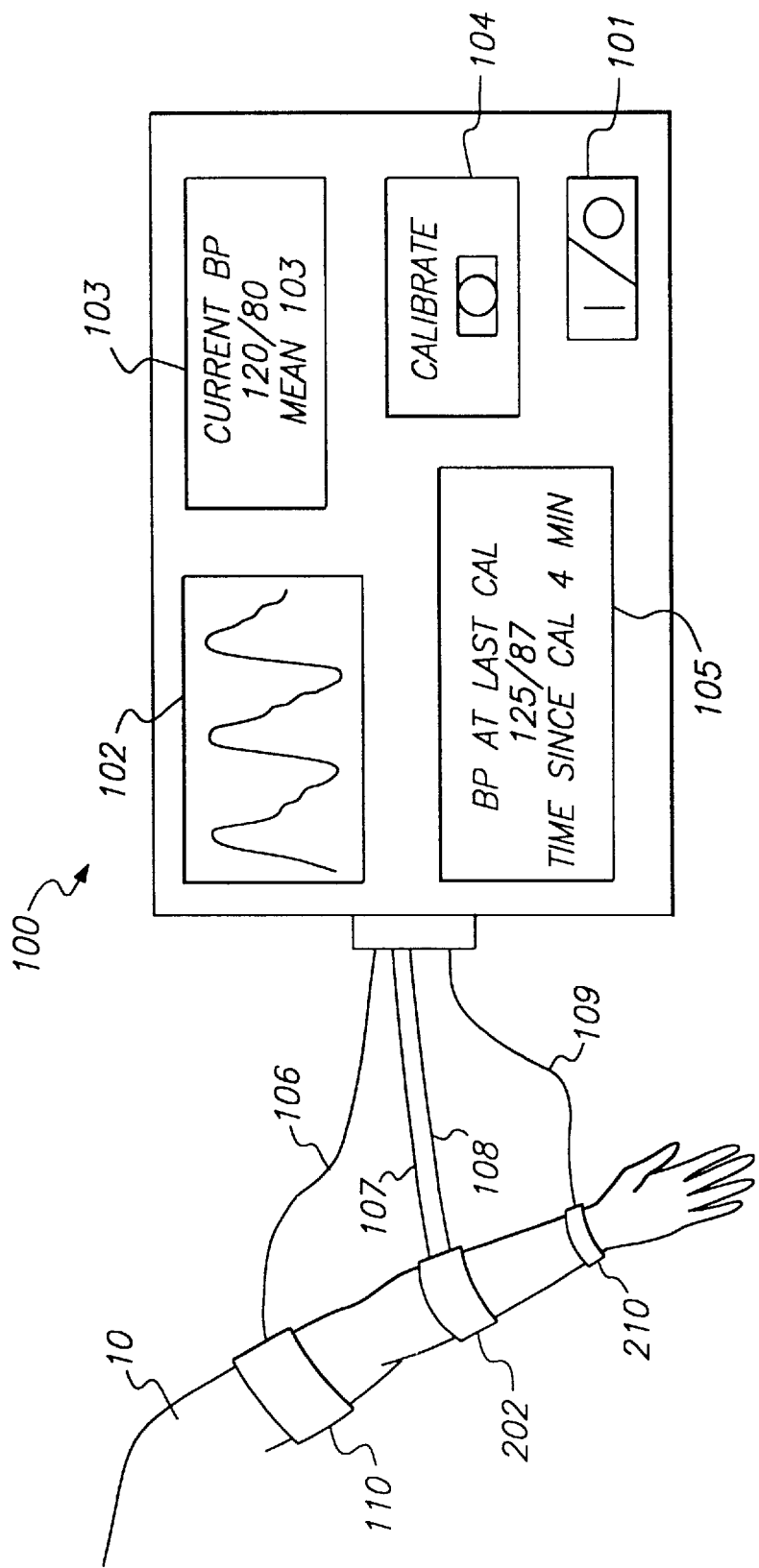
FIG. 1 depicts the present invention attached to a patient.

FIG. 1 illustrates the components and configuration of the preferred embodiment. Oscillometric cuff 110 is connected to processor 100 via wire 106, and cuff 110 is responsive to processor 100 during an initial calibration step. Oscillometric cuff operation, which is known in the art, involves an automated procedure for obtaining a blood pressure signal. The general procedure is given for clarity but is not crucial to the invention.

First, an occlusive cuff is pressurized around the patient's upper arm to abate the blood flow. Then, as the pressure is slowly reduced, a transducer senses when the blood flow begins and this pressure is recorded as the systolic pressure. As the pressure is further reduced, the transducer similarly detects the pressure when full blood flow is restored and this pressure is recorded as the diastolic pressure. The signals representing pressure are delivered, via wire 106, to processor 100 for storage. An alternative blood pressure measurement technique such as manual or automated sphygmomanometry using Korotkoff sounds or "return to flow" techniques, could also be used. A manual measurement can be provided, for example, using a keypad. Whatever measurement technique is used, a calibration device provides a calibration signal representative of the patient's physiological parameter. In this respect, the calibration device is broadly defined to include automated or manual measurements.

FIG. 1 shows an exciter 202 attached to the patient's forearm above the radial artery. The exciter 202 is a device for inducing a perturbation of the patient's body tissue, and is controlled by the processor 100 via tube 107.

Figure 2:
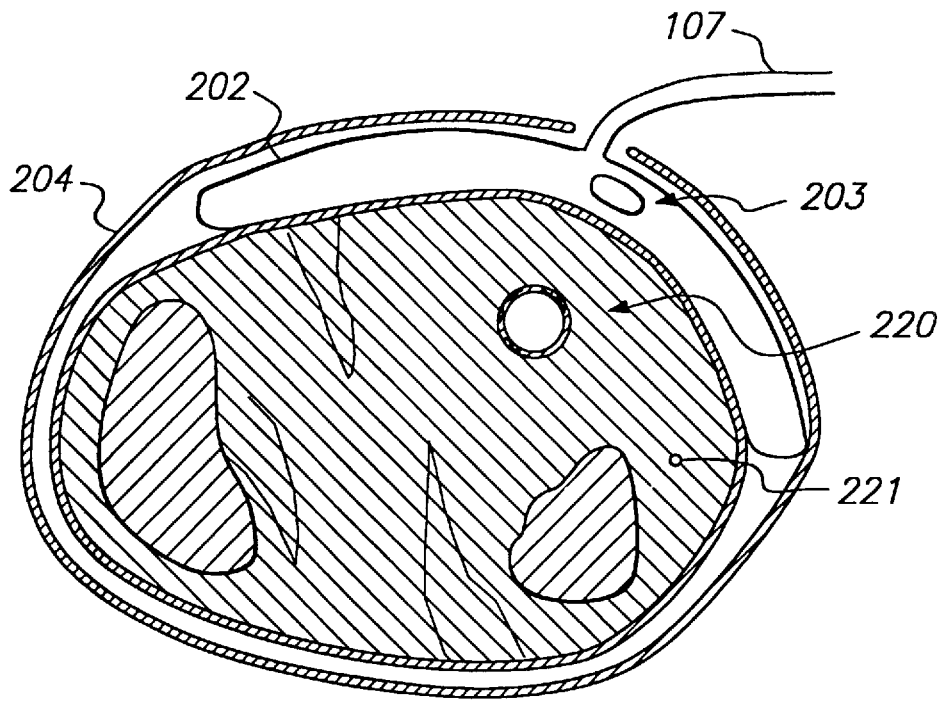
FIG. 2 depicts an exciter attached to a patient.

FIG. 2 shows a cross section of the exciter and its components. The exciter 202 is an inflatable bag attached to the processor via air tube 107. It is fixed in place near an accessible artery 220 by holddown device 204 which can be a buckle, adhesive strap or other device. There is also an exciter sensor 203 disposed within the exciter to generate a reference signal indicative of the perturbation source waveform, and to deliver the signal to the processor via wire 108. This signal is used as a reference signal by the processor (explained below).

As mentioned above, processor 100 is attached to the exciter via tube 107. The processor 100 controls the pressure in exciter 202 with a transducer and diaphragm. A transducer is a device that transforms an electrical signal to physical movement, and a diaphragm is a flexible material attached to the transducer for amplifying the movement. An example of this combination is a loudspeaker. The diaphragm forms part of an airtight enclosure connected to air tube 107 and an input to initialize the pressure. It will be clear to one skilled in the art that the transducer and air tube 107 and exciter 202 can be miniaturized and combined into a single exciter element capable of acting as a vibrating air filled bag connected to the processor by an electrical drive signal alone, in the case that a source of substantially constant pressure such as a spring is included in the exciter, or by an electrical drive signal and connection to a source of substantially constant pressure for the bag.

In operation, the pressure is initially established via the initialization input and then the pressure is varied by an electrical signal delivered to the transducer; the diaphragm produces pressure variations in the tube in response to the transducer movement. The result is that the processor, by delivering an oscillating electrical signal to the transducer, causes oscillating exciter pressure. The exciter responds by perturbing the patient's tissue and inducing a transmitted exciter waveform into the patient.

The perturbation excites the tissue 221 and blood vessel 220 below the exciter and causes the transmitted exciter waveform to radiate within the patient's body, at least a portion of which travels along the blood filled vessel. The excitation waveform can be sinusoidal, square, triangular, or of any suitable shape. Experiments conducted to determine a range of satisfactory perturbation frequencies found that the range of 20–1000 Hz works well. It is anticipated that frequencies of lesser than 20 Hz and greater than 1000 Hz will also work well, and it is intended that this specification cover all frequencies insofar as the present invention is novel.

FIG. 1 further shows a noninvasive sensor 210 placed at a distance from the exciter on the patient's wrist. The noninvasive sensor is connected to the processor 100 via wire 109.

Figure 3:
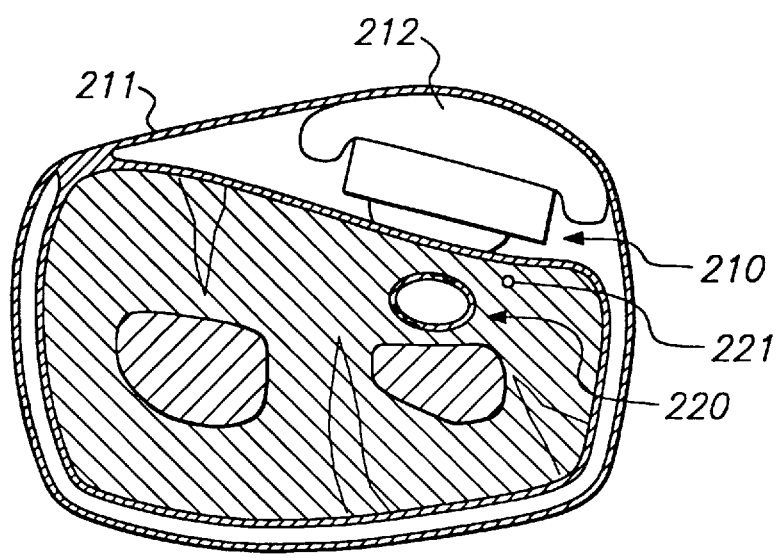
FIG. 3 depicts a noninvasive sensor attached to a patient.

FIG. 3 shows a cut-away view of the noninvasive sensor 210 placed over the same radial artery 220 as the exciter. The sensor 210 is fixed in place near the artery 220 by holddown device 211 which can be a buckle, adhesive strap or other device. The holddown device 211 also includes a baffle 212 to reduce noise, where the baffle is a pneumatic bag pressurized to hold the sensor 210 at a constant pressure against the patient, for example at a pressure of 10 mm Hg. Alternately, baffle 212 can be any suitable device such as a spring or foam pad.

The noninvasive sensor 210 is responsive to at least one hemoparameter of the patient and generates a signal in response thereto. In this context, a hemoparameter is defined as any physiological parameter related to vessel blood such as pressure, flow, volume, velocity, blood vessel wall motion, blood vessel wall position and other related parameters. In the preferred embodiment a piezoelectric sensor is used to sense arterial wall displacement, which is directly influenced by blood pressure.

As is shown, the sensor is positioned over the radial artery 220 and it is responsive to pressure variations therein; as the pressure increases, the piezoelectric material deforms and generates a signal corresponding to the deformation. The signal is delivered to the processor 100 via wire 109.

FIG. 1 also shows the processor 100 that has a control panel for communicating information with the user. A power switch 101 is for turning the unit on. A waveform output monitor 102 displays the continuous blood pressure waveform for medical personnel to see. This waveform is scaled to the pressures determined by the processor, and output to the monitor. A digital display 103 informs the user of the current blood pressure; there is a systolic over diastolic and mean pressure shown. A calibrate button 104 permits the user to calibrate the processor at any time, by pressing the button. The calibration display 105 shows the user the blood pressure at the most recent calibration, and also the elapsed time since calibration. The processor maintains a record of all transactions that occur during patient monitoring including calibration blood pressure, calibration times, continuous blood pressure and other parameters, and it is anticipated that additional information can be stored by the processor and displayed on the control panel.

Turning to the noninvasive sensor signal, in addition to a natural hemoparameter, the noninvasive sensor signal contains a component indicative of the exciter waveform traveling through the patient. Although the exciter component is designed to be small in comparison to the natural hemoparameter, it contains valuable information. Therefore, the processor is used to separate the exciter waveform from the natural hemoparameter, and to quantify the respective components to determine the patient's blood pressure.

Figure 4A:
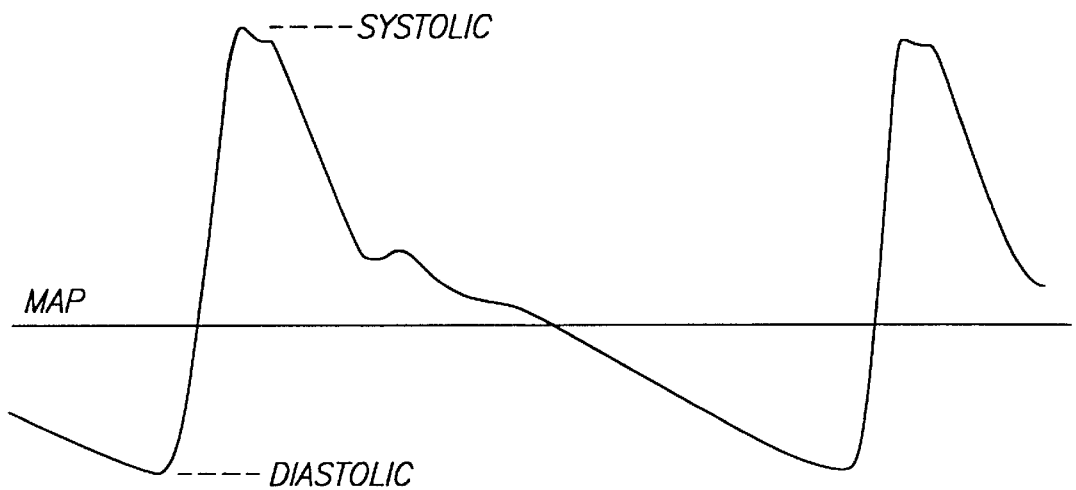
FIG. 4a depicts a blood pressure waveform.

FIG. 4a shows a natural blood pressure waveform where the minimum represents the diastolic pressure and the maximum represents the systolic pressure. This waveform has a mean arterial pressure (MAP) that is a convenient reference for purposes of determining the DC offset of the waveform. Example pressure values are 80 mm Hg diastolic and 120 mm Hg systolic respectively with a MAP DC offset of 90 mm Hg.

Figure 4B:
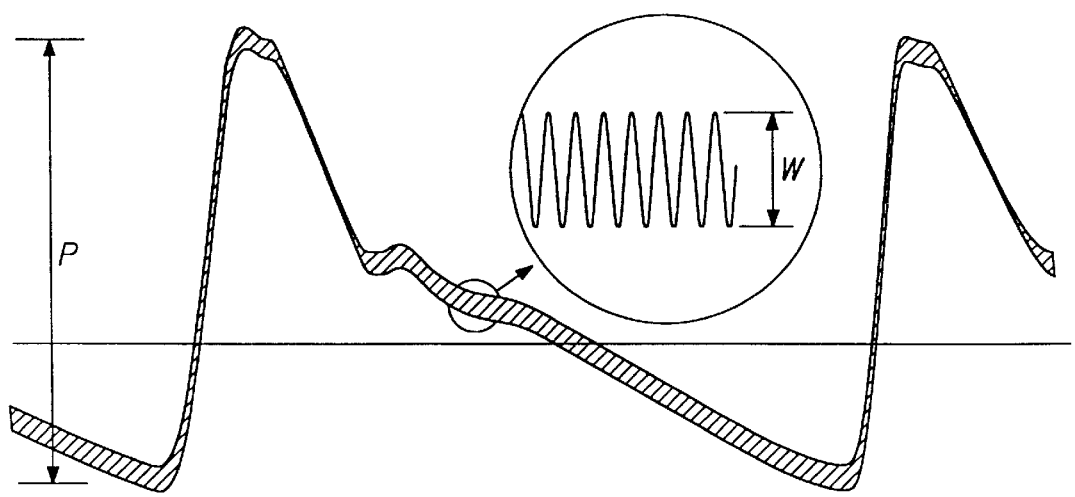
FIG. 4b depicts a blood pressure waveform with an exciter waveform superimposed thereon.

FIG. 4b shows an operational illustration of the arterial waveform; an exciter waveform superimposed on a natural blood pressure waveform. The exciter induces the exciter waveform into the arterial blood at a first location and the exciter waveform becomes superimposed on the natural waveform. Since the exciter waveform is small compared to the patient's natural waveform, the natural waveform dominates as shown in FIG. 4b. As mentioned above, the noninvasive sensor signal contains information regarding both the natural waveform and the exciter waveform. The processor 100 is designed to separate the constituent components of the noninvasive sensor signal to continuously determine the patient's blood pressure, as is discussed below.

FIG. 5 depicts a schematic diagram of the preferred embodiment. There is an oscillometric cuff controller 121 for controlling the oscillometric cuff and determining the readings therefrom to generate a signal representing the patient's blood pressure. There is an induced wave frequency generator 131 coupled to a pressure transducer 133 that transforms an electrical input to a pressure output. The transducer output is connected to the exciter 202 and controls the exciter's oscillations for inducing the exciter waveform into the patient's arterial blood.

The output of the exciter sensor 203 is fed to a band pass filter 134. This filter 134 separates the high frequency signal responsive to the transducer pressure and delivers the resulting signal to RMS meter 135 and to lock-in amplifier 143 reference input. In the preferred embodiment, the RMS meter output is sampled at a rate of 200 samples per second with a 14 bit resolution and delivered to computer 150. It is anticipated that the sampling rate and resolution can be varied with good results.

The output of the noninvasive sensor is fed to a charge amplifier 140 that delivers a resulting signal to a low pass filter 141 and a band pass filter 142. These filters separate the noninvasive sensor signal into two constituent components representing an uncalibrated natural blood pressure wave and a received exciter waveform respectively. The low pass filter output is sampled at a rate of 200 samples per second with 14 bit resolution and delivered to computer 150, and the band pass filter output is delivered to the lock-in amplifier 143 signal input.

The lock-in amplifier 143 receives inputs from band pass filter 134 as reference and band pass filter 142 as signal, which are the exciter sensor signal (transmitted exciter waveform) and noninvasive sensor exciter signal (received exciter waveform) respectively. The lock-in amplifier uses a technique known as phase sensitive detection to single out the component of the noninvasive sensor exciter signal at a specific reference frequency and phase, which is that of the exciter sensor signal. The amplifier 143 produces an internal, constant-amplitude sine wave that is the same frequency as the reference input and locked in phase with the reference input. This sine wave is then multiplied by the noninvasive sensor exciter signal and low-pass filtered to yield a signal proportional to the amplitude of the noninvasive sensor signal multiplied by the cosine of the phase difference between the noninvasive exciter signal and the reference. This is known as the in-phase or real output.

The amplifier 143 also produces an internal reference sine wave that is 90 degrees out-of-phase with the reference input. This sine wave is multiplied by the received exciter signal and low-pass filtered to yield a signal proportional to the amplitude of the noninvasive sensor signal multiplied by the sine of the phase difference between the noninvasive sensor exciter signal and the reference. This is known as quadrature or imaginary output. The amplifier 143 then provides the computer 150 with information regarding the real and imaginary components of the received exciter signal as referenced to the phase of the transmitted exciter signal. Alternately, the amplifier can provide components representing the magnitude and phase of the received exciter signal. In the preferred embodiment, the amplifier output is sampled at a rate of 200 samples per second with a 14 bit resolution. It is anticipated that the sampling rate and resolution can be varied with good results.

The computer 150 receives input from the oscillometric cuff controller 121, RMS meter 135, low pass filter 141 and lock-in amplifier 150. The computer 150 also receives input from the user interface panel 160 and is responsible for updating control panel display information. The computer 150 executes procedures for further separating constituent components from the noninvasive sensor signal and attenuating the noninvasive sensor noise component as shown in FIG. 6.

While the processing system described in the embodiments involves the use of a lock-in amplifier 143, it will be clear to those persons skilled in the art that similar results can be achieved by frequency domain processing. For example, a Fourier transform can be performed on the various signals to be analyzed, and processing in the frequency domain can be further performed that is analogous to the described processing by the lock-in amplifier in the time domain. The various filtering steps described above can be advantageously performed in the frequency domain. Processing steps in the frequency domain are considered as falling within the general category of the analysis of the transfer function between the exciter sensor waveform and the noninvasive sensor waveform and are intended to be covered by the claims. The variety of techniques that are used in the art for the calculation of transfer functions are also applicable to this analysis.

PROCESS EXCITER WAVEFORM VELOCITY TO DETERMINE OFFSET SCALING AND EXCITER WAVEFORM AMPLITUDE TO DETERMINE GAIN SCALING

Figure 6A:
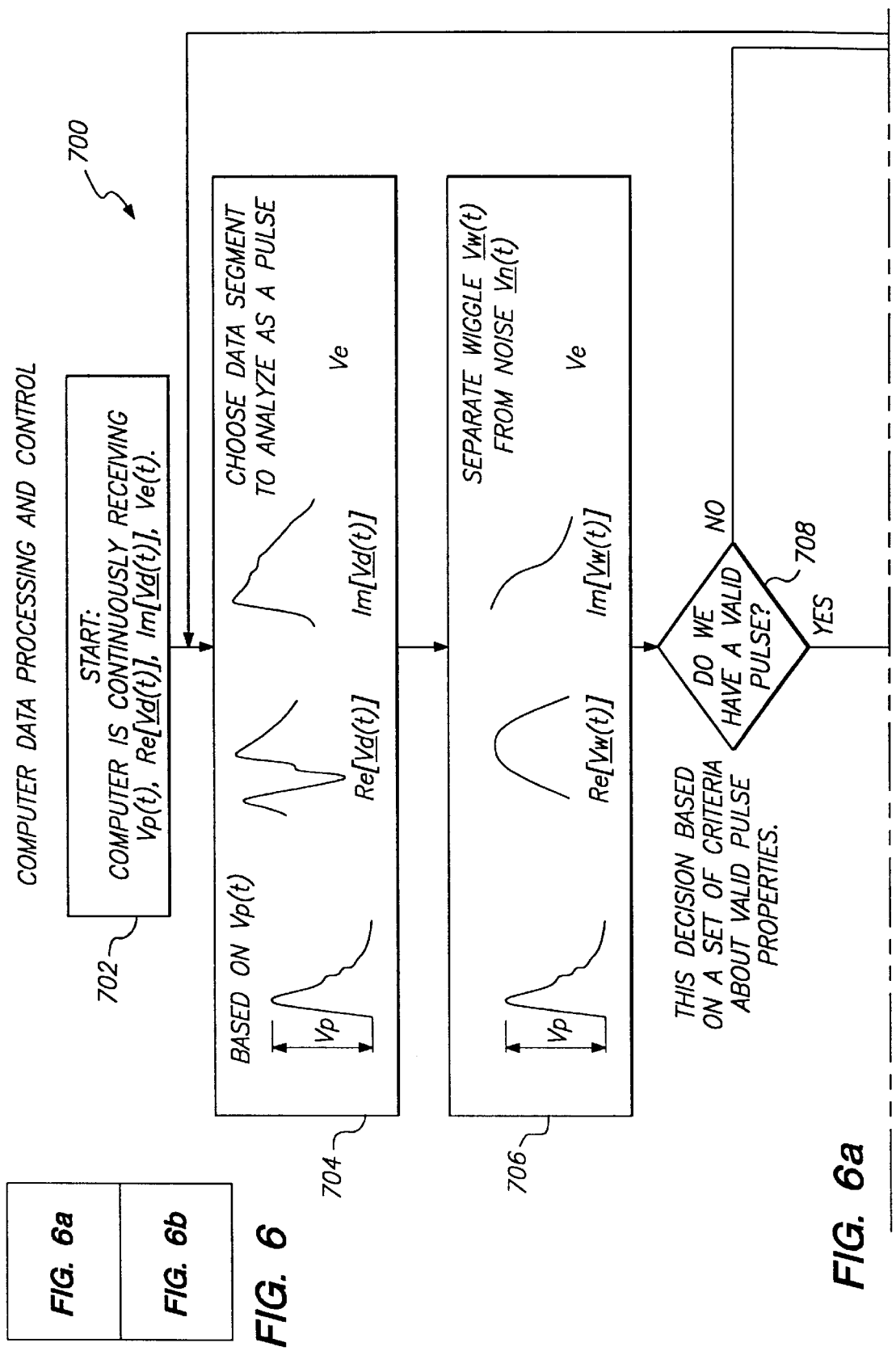
FIGS. 6a–b depict a processing flow chart according to one embodiment of the invention.
Figure 6B:
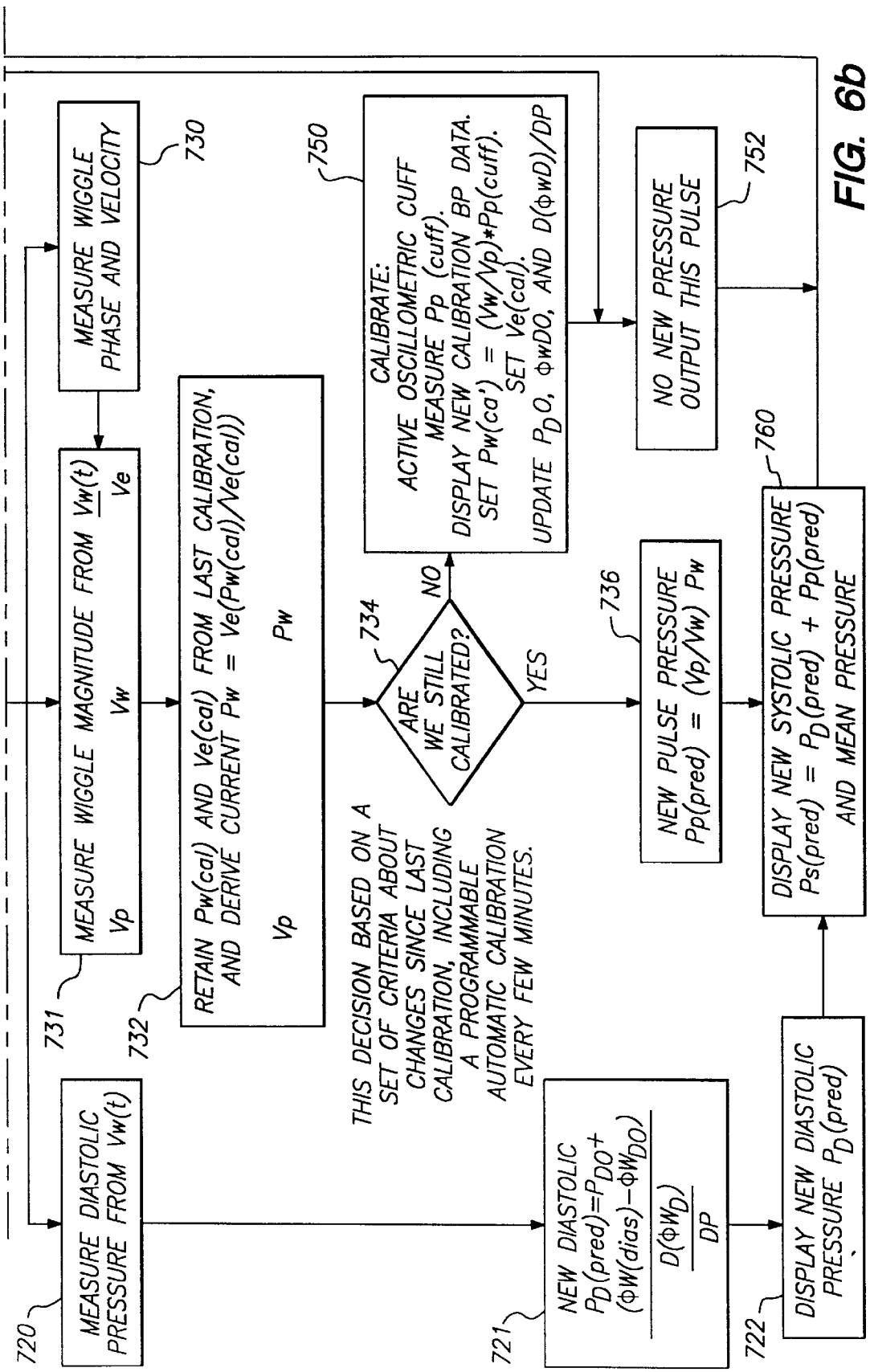

FIG. 6 is a processing flowchart that represents the operation of the FIG. 5 computer 150. The operation begins at step 702 with the receipt of an initial calibration measurement; noninvasive sensor signal and exciter sensor signal. Step 704 chooses the blood pressure waveform segment for pulse reference, which is important for continuity of measurement from pulse to pulse and for consistency over periods of time between calibration measurements. In this embodiment, the diastolic pressure (low-point) is chosen for purposes of simplicity, but any point of the waveform can be chosen such as the systolic pressure or mean arterial pressure (MAP). The choice of the segment will relate to the DC offset discussed below.

Step 706 is a filter step where the noninvasive sensor (received) exciter waveform is separated into signal and noise components. The noise components may have many sources, one of which is a signal derived from the exciter that travels to the noninvasive sensor by an alternate path, other than that along the artery taken by the signal of interest. Examples include bones conducting the exciter waveform and the surface tissue such as the skin conducting the exciter waveform. Additional sources of noise result from patient movement. Examples include voluntary patient motion as well as involuntary motion such as movement of the patient's limbs by a physician during surgery.

Figure 7A:
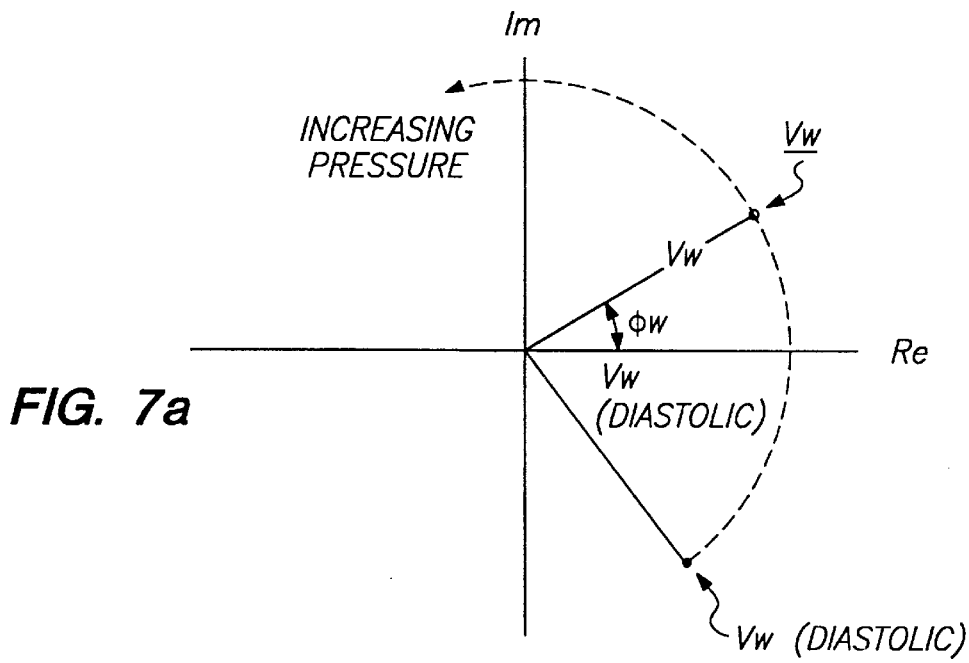
FIGS. 7a–c are graphical illustrations of the filter procedures of the present invention.
Figure 7B:
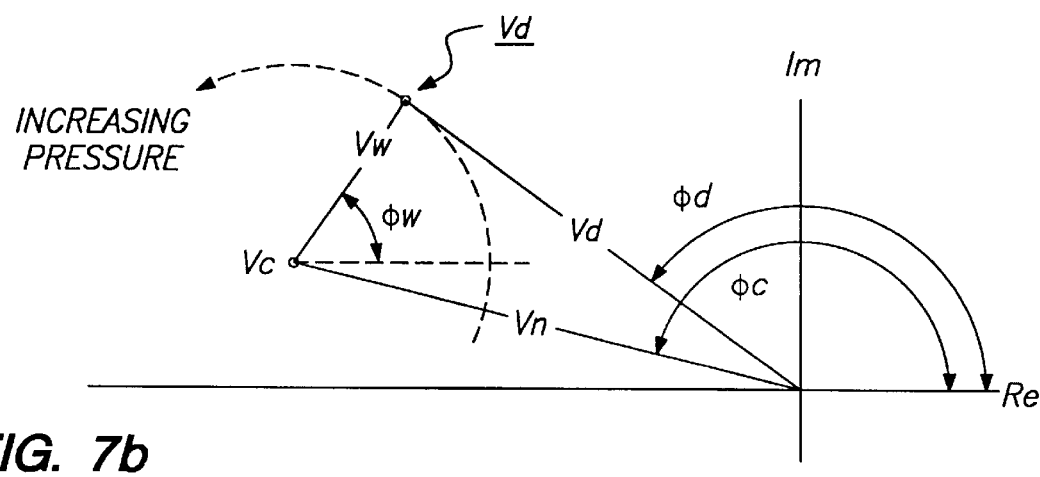
Figure 7C:
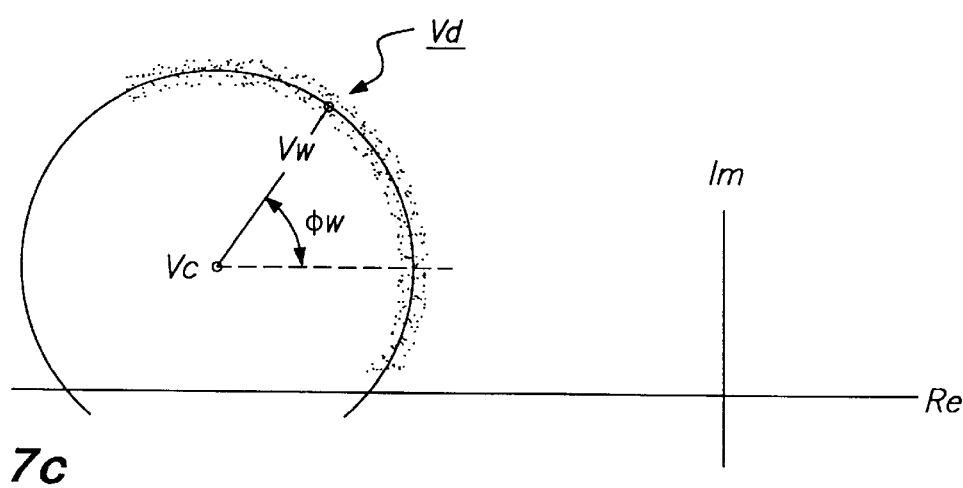

FIGS. 7a–c illustrate the principles of the received exciter signal filtering. During a natural pulse, the received exciter waveform $V_d$ is represented by a collection of points that are generated in the complex plane by the real and imaginary outputs of the lock-in amplifier 143 which is monitoring the noninvasive sensor signal. FIG. 7a represents the received exciter waveform $V_d$ in the absence of noise. In the absence of noise, $V_d$ is the same as vector $V_w(t)$ which has a magnitude and phase corresponding to the received exciter signal. During a pulse, the magnitude of $V_w(t)$ remains constant, but the angle periodically oscillates from a first angle representing a lesser pressure to a second angle representing a greater pressure. Note that in the absence of noise, the arc has a center at the origin.

FIG. 7b represents the received exciter waveform $V_d$ in the presence of noise, which is indicated by vector $V_n$. Vector $V_d$ has a magnitude and phase according to the noninvasive sensor exciter waveform plus noise. As can be seen in FIGS. 7b–c, vector $V_d(t)$ defines a collection of points forming an arc having a common point $V_c$ equidistant from each of the collection of points. The vector $V_w(t)$ from $V_c$ to the arc corresponds to the true magnitude and phase of the noninvasive signal exciter waveform. The vector $V_n$ represents noise and, once identified, can be removed from the noninvasive sensor waveform. The filter step removes the $V_n$ noise component and passes the $V_w(t)$ signal exciter component on to step 708.

In the above discussion, it was assumed for illustrative purposes that the magnitude of $V_w(t)$ remains constant over the time of a pulse. In some cases the attenuation of the exciter waveform as it propagates along the artery is pressure dependent, and in those cases the magnitude of $V_w(t)$ can vary during the pulse in a way that is correlated to pressure. Under such circumstances the shape of the figure traced out in the complex plane by the vector $V_d$ will deviate from a perfect circle segment. A typical shape is that of a spiral with a form that can be predicted theoretically. The functioning of this filter step under such circumstances is conceptually similar to that described above, except that the elimination of the noise vector $V_n$ must involve location of the origin of a spiral rather than of the center of a circle.

Step 708 determines if the pulse is valid. To do this, the processor checks the constituent components of the noninvasive sensor signal to insure that the components are within acceptable clinical norms of the patient. For example, the processor can determine whether the new pulse is similar to the prior pulse, and if so, the new pulse is valid.

Figure 8A:
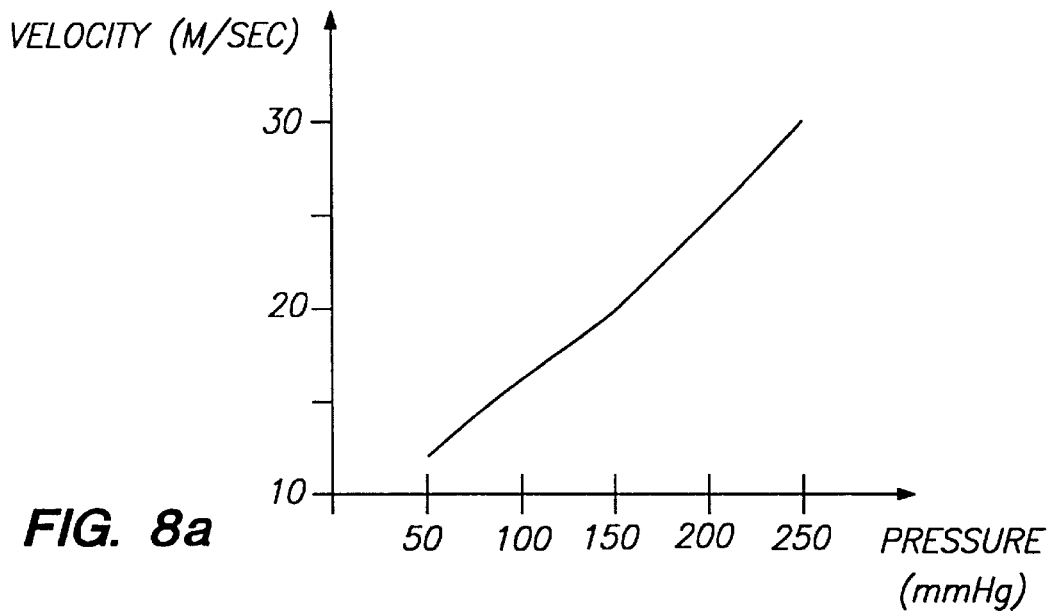
FIGS. 8a–c are graphical illustrations showing the relationships between the exciter waveform and blood pressure.
Figure 8B:
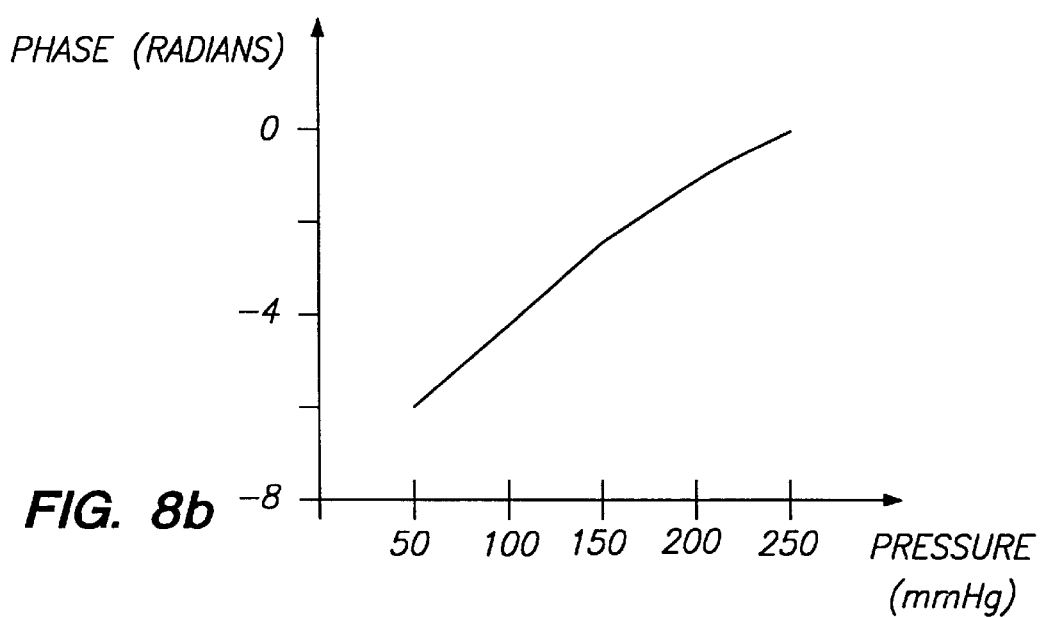
Figure 8C:
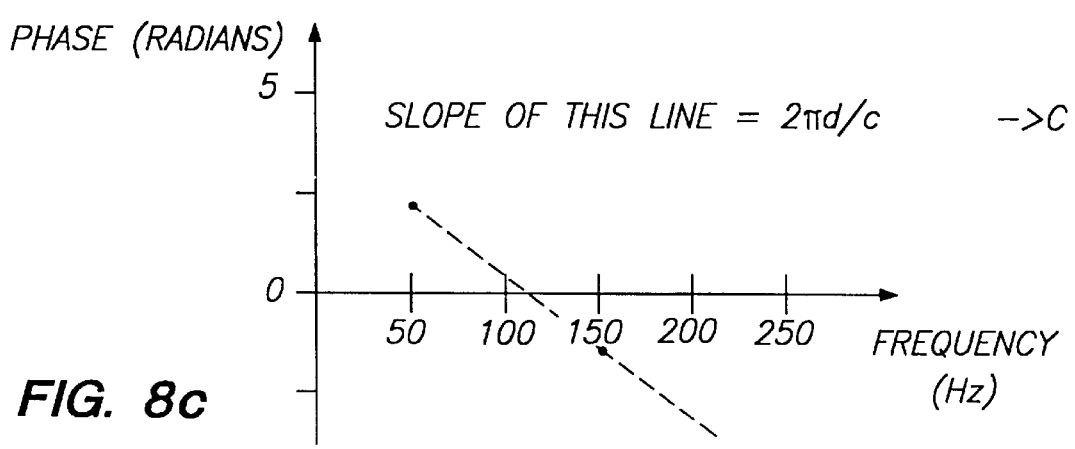

Step 720 processes the signal exciter waveform $V_w(t)$ to determine the DC offset. For convenience the diastole is used as the offset value, but any part of the waveform can be used. The processor determines the offset when the vector $V_w(t)$ reaches its lowest phase angle (i.e., the maximum clockwise angle of FIG. 7a); this is the diastole phase angle $\Phi w(dias)$. A calibration diastolic measurement is stored by the processor at calibration as $P_{D0}$. Also stored by the processor is a relationship denoting the relationship between the velocity of an exciter wave and blood pressure. This relationship is determined by reference to a sample of patients and is continuously updated by reference to the particular patient after each calibration measurement. FIGS. 8a–c are graphical illustrations showing clinically determined relationships between the exciter waveform and blood pressure. FIG. 8b represents the relationship between phase and pressure at a frequency of 150 Hz; other frequencies have relationships that are vertically offset from the line shown. The pressure-velocity relationship represents the storage of this graphical information either in a data table or by an analytical equation.

Step 721 determines the predicted diastolic pressure from the information in Step 720. The processor continuously determines the change in diastole from one pulse to the next by referencing the position of the signal exciter vector $V_w(t)$, at $\Phi w(dias)$, with respect to the stored pressure-velocity relationship. Moreover, the pressure-velocity relationship is continuously updated based on calibration measurement information gained from past calibrations of the patient.

A set of established relationships is used to develop and interpret information in the table and to relate the information to the sensor signal components. First, a known relationship exists between blood pressure and exciter waveform velocity. Also, at a given frequency many other relationships are known: a relationship exists between velocity and wavelength, the greater the velocity the longer the wavelength; and a relationship exists between wavelength and phase, a change in wavelength will result in a proportional change in phase. Hence, a relationship exists between blood pressure and phase, and a change in blood pressure will result in a proportional change in phase. This is the basis for the offset prediction.

With the stored calibration measurement plus the change in diastole, the new DC offset diastolic pressure is predicted $P_D(pred)$. This prediction is made based on the diastolic pressure at calibration $P_{D0}$ plus the quotient of the phase difference between calibration $\Phi w_{D0}$ and the present time $\Phi w(dias)$ and the pressure-velocity relationship stored in processor memory as rate of change of exciter waveform phase to pressure $d(\Phi w_D)/dP$.

$$P_D(pred) = P_{D0} + \frac{(\Phi w(dias) - \Phi w_{D0})}{d(\Phi w_D)/dP} \quad (2)$$

Step 722 displays the predicted diastolic pressure.

Step 730 determines the noninvasive sensor exciter waveform phase and velocity. This determination is made based on the comparison of the noninvasive sensor exciter waveform with the exciter sensor waveform.

Step 731 determines the noninvasive sensor exciter waveform amplitude from the noninvasive sensor signal.

Step 732 determines the exciter waveform pressure $P_w$ by multiplying the exciter sensor waveform magnitude $V_e$ by the ratio of the calibrated exciter waveform pressure $P_w(cal)$ to the calibrated exciter sensor waveform magnitude $V_e(cal)$.

$$P_w = V_e * \frac{P_w(cal)}{V_e(cal)} \quad (3)$$

In situations where a significant pressure variation can be observed in the attenuation of the exciter waveform as it propagates from exciter to detector, an additional multiplicative pressure dependent correction factor must be included in equation 2.

Step 734 determines if the calibration values are still valid. This determination can be based on many factors including the time since the last calibration, that the linearity of the pressure-velocity relationship is outside of a reliable range, determination by medical personnel that a new calibration is desired or other factors. As an example of these factors, the preferred embodiment provides user settable calibration times of 2, 5, 15, 30, 60 and 120 minutes, and could easily provide more. Moreover, the curve upon which the pressure is determined is piecewise linear with some degree of overall nonlinearity. If the processor 100 determines that the data is unreliable because the linear region is exceeded, the processor will initiate a calibration step. Finally, if the operator desires a calibration step, a button 104 is provided on the processor 100 for initiating calibration manually.

Step 736 predicts a new pulse pressure $P_p(pred)$ by multiplying the exciter waveform pressure $P_w$ by the ratio of the detected pulsatile voltage $V_p$ to the detected exciter waveform magnitude $V_w$.

$$P_p(pred) = P_w * \left(\frac{V_p}{V_w}\right) \quad (4)$$

This prediction uses the noninvasive sensor exciter waveform to determine the pressure difference between the diastole and systole of the natural blood pressure waveform. For example, if a noninvasive sensor exciter magnitude $V_w$ of 0.3 V relates to a pressure variation $P_w$ of 1 mm Hg and the noninvasive sensor waveform $V_p$ varies from −6 V to +6 V, then the noninvasive sensor waveform represents a pulse pressure excursion $P_p(pred)$ of 40 mm Hg.

Step 760 predicts a new systolic pressure P(pred) by adding the predicted diastolic $P_D(pred)$ and pulse pressures $P_p(pred)$.

$$P_s(\text{pred}) = P_D(\text{pred}) + P_p(\text{pred}) \quad (5)$$

In the above example if the diastole $P_D(\text{pred})$ is 80 mm Hg (DC offset) and the pulse $P_p(\text{pred})$ represents a difference of 40 mm Hg then the new systolic $P_s(\text{pred})$ is 120 mm Hg. Then the new systolic pressure is displayed.

For display purposes the values determined for $P_S(\text{pred})$ and $P_D(\text{pred})$ can be displayed numerically. Similarly, the output waveform for display 102 can be displayed by scaling the noninvasive sensor natural blood pressure waveform prior to output using gain and offset scaling factors so that the output waveform has amplitude, $P_p(\text{pred})$, and DC offset, $P_D(\text{pred})$, equal to those predicted in the above process. The scaled output waveform signal can also be output to other instruments such as monitors, computers, processors and displays to be used for display, analysis or computational input.

Step 750 is taken when step 734 determines that the prior calibration is no longer reliable as described above. A calibration step activates the oscillometric cuff 201 and determines the patient's blood pressure, as described above. The processor 100 uses the calibration measurements to store updated pressure and waveform information relating to the DC offset, blood pressure waveform and exciter waveform. The updated variables include calibration pulse pressure $P_p(\text{cal})$, calibration exciter sensor waveform magnitude $V_e(\text{cal})$, diastolic pressure $P_{D0}$, diastolic exciter waveform phase $\Phi w_{D0}$, the rate of change of exciter waveform phase to pressure $d(\Phi w_D)/dP$ and calibration exciter waveform pressure $P_w(\text{cal})$.

$$P_w(cal) = P_p(cal) * \left(\frac{V_w}{V_p}\right) \quad (6)$$

PROCESS EXCITER WAVEFORM VELOCITY TO DETERMINE OFFSET SCALING AND GAIN SCALING

Figure 9B:
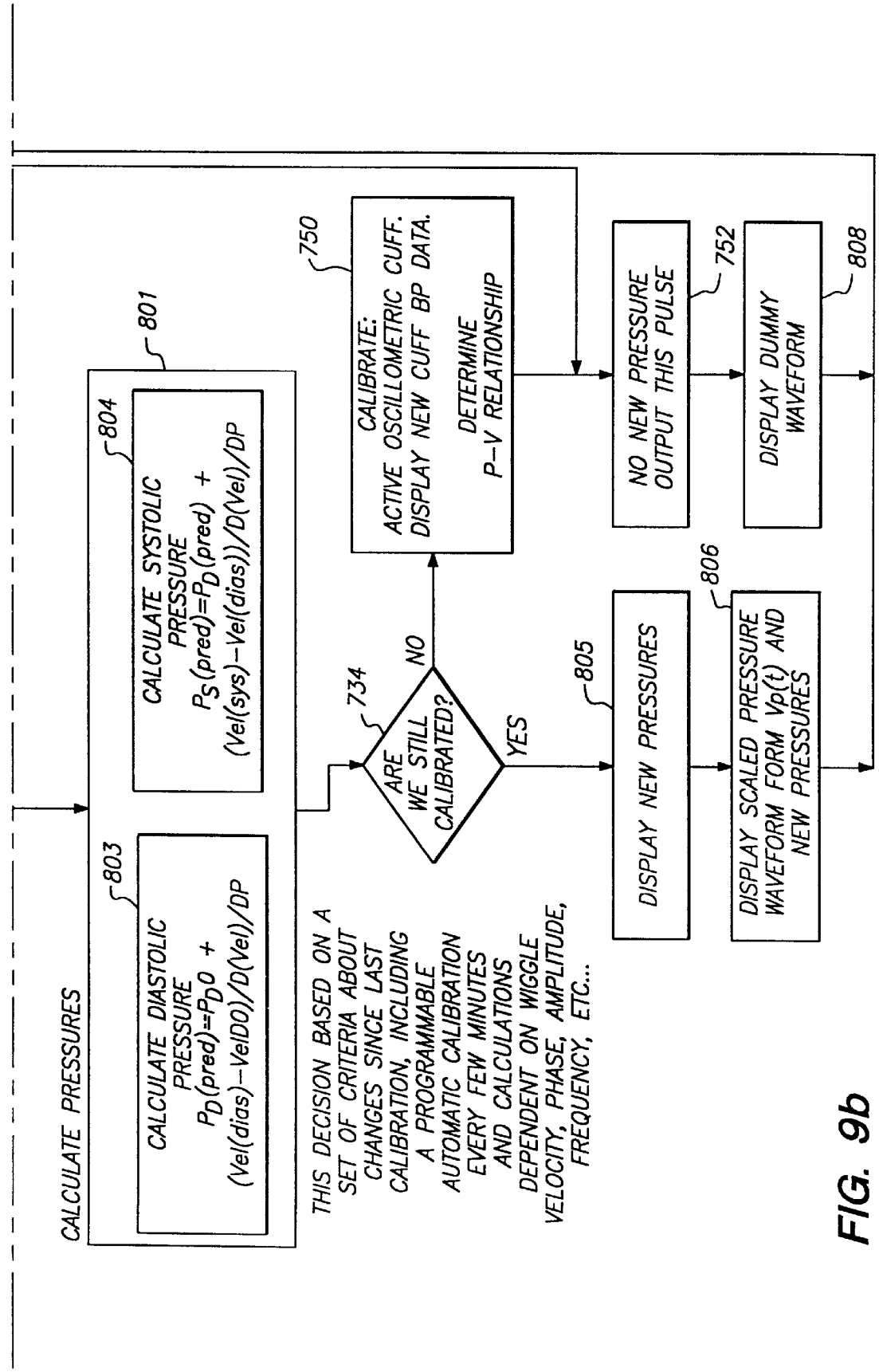
FIGS. 9a&b depict a processing flow chart according to another embodiment of the invention.

FIGS. 9a–b represent a modification to the previous embodiment. The initial processing steps 702, 704, 706, 708, 730 and 731 represented in the flow chart of FIG. 9 are substantially similar to those described in the previous embodiment depicted in FIG. 6. In step 730, exciter waveform velocity Vel(t) and the actual phase delay of the exciter waveform $\Phi(t)$ are related by the equation:

$$\Phi(t) = \Phi_0 - 2\pi df/\text{Vel}(t) \quad (6)$$

where frequency f and distance d between exciter and noninvasive sensor are known. The constant $\Phi_0$ is determined in advance either analytically or empirically, and is dependent on the details of the geometry of the apparatus.

Measurement of $\Phi(t)$ is generally made modulo $2\pi$, and so the measured phase $\Phi_m(t)$ is related to actual phase delay by the equation:

$$\Phi_m(t) = \Phi(t) + 2n\pi \quad (7)$$

where n is an integer also known as the cycle-number, typically in the range of 0–10. While correct deduction of propagation velocity requires a correct choice of n, a correct prediction of pressure using a pressure-velocity relation does not, so long as the same value of n is used in determining $\Phi(t)$ and in determining the pressure-velocity relationship. In such a case, velocity should be considered as a pseudo-velocity rather than an actual measure of exciter waveform propagation speed.

In step 730, therefore, use of the $\Phi(t)$ equations allows determination of the velocity, or pseudo-velocity, Vel(t) as a function of time. In step 801, the values of velocity at the systolic and diastolic points of the cardiac cycle are determined as $\text{Vel}_S$ and $\text{Vel}_D$. These correspond to the points of minimum and maximum phase delay or to the points of maximum and minimum amplitude of the naturally occurring blood pressure wave detected by the noninvasive sensor. Use of the pressure-velocity relationship stored in the processor is then made to transform the values of velocity at systolic and diastolic points in time to values of pressure. In step 803 the diastolic pressure is determined using the equation:

$$P_D(\text{pred}) = P_{D0} + (\text{Vel}_D - \text{Vel}_{D0})/(d\text{Vel}/dP) \quad (8)$$

Step 804 is performed to determine the predicted systolic pressure according to the relationship:

$$P_S(\text{pred}) = P_D(\text{pred}) + (\text{Vel}_S - \text{Vel}_D)/(d_{Vel/dP}) \quad (9)$$

In this illustration the values of $P_S$ and $P_D$ are used to determine the pressure waveform. Similarly, other pairs of values, such as mean pressure and pulse pressure can also be used, and appropriate permutations of the predicted pressure equations are anticipated by this description.

In step 805 the calculated pressures are displayed as numbers, with a typical display comprising display of mean, systolic and diastolic values of the pressure waveform in digital form, together with the observed pulse rate. The values of $P_D(\text{pred})$ and $P_S(\text{pred})$ are used to determine appropriate gain and DC offset scaling parameters by which the naturally occurring blood pressure waveform detected by the noninvasive sensor is scaled prior to output in step 806 as a time varying waveform, shown as 102 in FIG. 1.

As in the embodiment depicted in FIG. 6, step 750 involves a calibration step initiated when step 734 determines that the prior calibration is no longer reliable. During the performance of step 750 the pressure-velocity relationship is determined and stored in the processor in the form of a table or of an analytical relationship. During this process, it may be desirable to stop the output portion of the process as shown in step 752 and display a different signal, such as a blank screen, a dashed line display, a blinking display, a square wave, or some other distinguishable signal of calibration such as an audible tone. This step is represented as step 808 in FIG. 9.

PROCESS EXCITER WAVEFORM VELOCITY TO DETERMINE OUTPUT BLOOD PRESSURE WAVEFORM

Figure 10B:
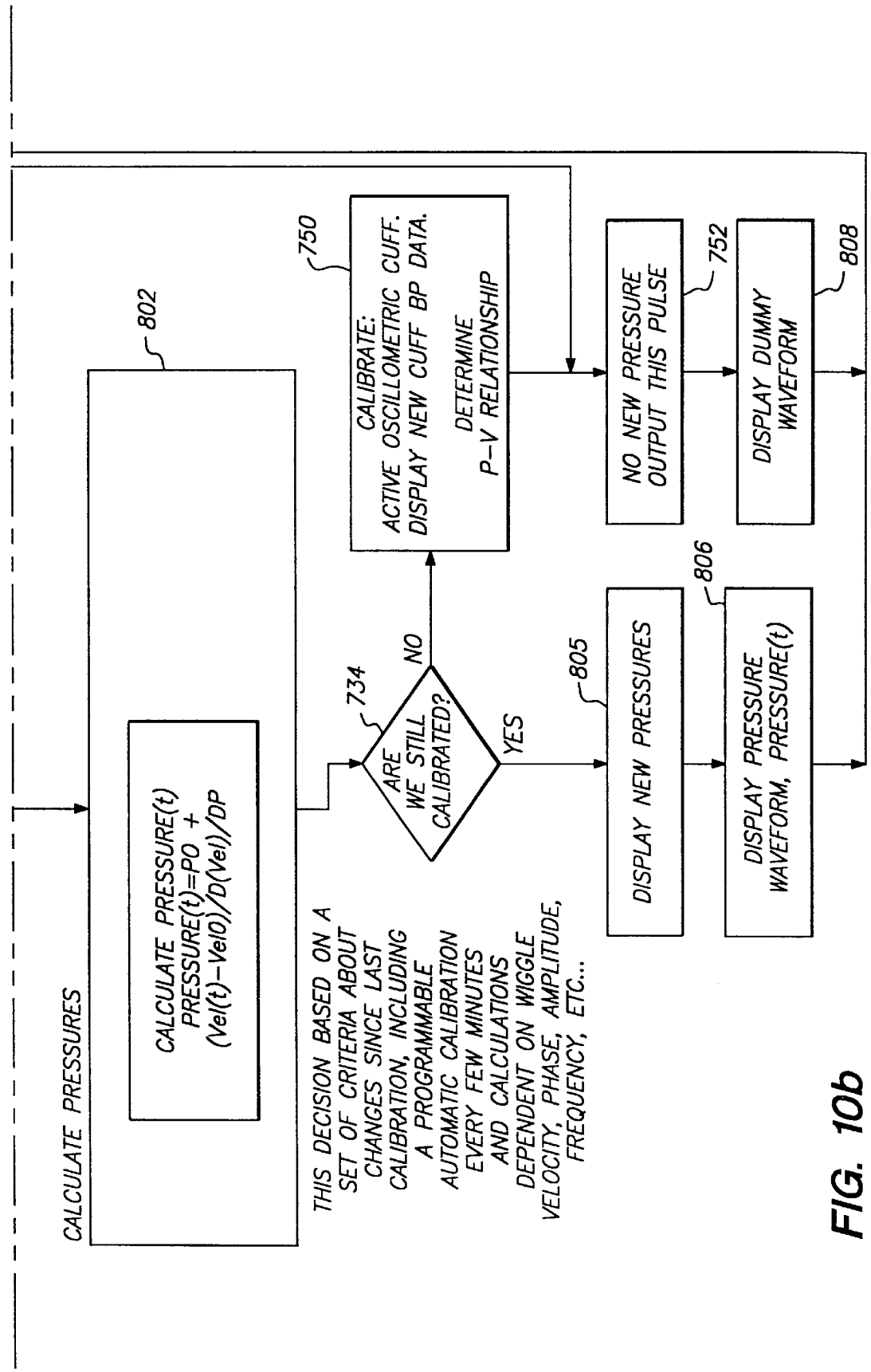
FIGS. 10a&b depict a processing flow chart according to another embodiment of the invention; and, FIG. 11 depicts an exciter and noninvasive sensor attached to a patient.

In both of the previous two embodiments, values of gain Pp(pred) and offset $P_D(\text{pred})$ are determined and used to scale the noninvasive sensor natural blood pressure waveform to provide a time varying output waveform representative of the patient's blood pressure. In this embodiment, the natural blood pressure waveform monitored by the noninvasive sensor is not used in the determination of the output blood pressure waveform. As in the previous embodiment, use is made of the relationship between velocity of the exciter waveform and the blood pressure of the patient to determine the blood pressure. Rather than making such a pressure determination only at the diastolic and systolic points of the cardiac cycle, exciter waveform velocity is measured many times during a cardiac cycle (typically 50–200 times per second) and the resultant determinations of pressure are used to construct the output time varying blood pressure waveform. This process is described below with reference to FIG. 10.

In this embodiment, the natural blood pressure waveform is not scaled. Therefore, there is no need to separate the data into pulse segments as in step 704 of FIG. 6. This feature greatly simplifies the computational task. An additional advantage of this technique is that all of the information used in the analysis process is encoded in the exciter waveform, which is typically at a high frequency compared with that of both the natural blood pressure waveform and that of any artifact signals introduced by patient motion or respiration. Since all of these lower frequency signals can be removed by electronic filtering, this technique is extremely immune to motion induced artifact and similar sources of interference that might otherwise introduce errors into the measurement.

With the exception of this step, the initial processing steps 702, 706, 731 and 730 are substantially similar to those of previously described embodiments. The amplitude and phase of the exciter waveform determined in step 731 are continuous functions of time. The exciter waveform phase is converted to exciter waveform velocity as described previously, which is also a continuous function of time.

Using a relationship between pressure and velocity, determined during or subsequent to the initial calibration and periodically redetermined, the time dependent velocity function Vel(t) is readily transformed to a time dependent pressure function P(t). This transformation is represented by step 802. In a typical case, the pressure-velocity relationship might be as follows:

$$Vel(t)=a+bP(t) \quad (10)$$

where the constants a and b were determined during step 750. In that case the velocity equation (10) can be used to perform the transformation of step 802.

Following a variety of checking steps, described below, that ensure the transformation used in 802 was correct, the minimum and maximum points of P(t) are determined for each cardiac cycle and displayed as $P_D$(pred) and $P_S$(pred) in step 805. Then, in step 806, the entire time dependent waveform is displayed as waveform 102.

DETERMINATION OF THE PRESSURE-VELOCITY RELATIONSHIP

In each of the embodiments described thus far, an important step involves the conversion of a measured phase to a deduced exciter waveform velocity, and conversion of that value to a pressure. In the case of the flow chart of FIG. 6, this process is integral to the calculation of the DC offset pressure $P_{D0}$. In the case of the embodiment described in FIG. 9, this process is integral to determination of $P_S$ and $P_D$. In the case of the embodiment described in FIG. 10, the process is integral to the determination of pressure at each point in time for which an output value is to be displayed as part of a "continuous" pressure waveform display.

The relationship between pressure and velocity is dependent on many factors including the elastic properties of the artery along which the exciter waveform travels. This relationship varies considerably between patients, and must therefore be determined on a patient by patient basis, although a starting relationship derived from a pool of patients can be used. This determination occurs during step 750 in each of the embodiments described in FIGS. 6, 9, and 10, and the relationship is stored in the processor in either a tabular form, or as an analytical relationship. In step 734 in FIGS. 6, 9 and 10, a variety of parameters are examined to determine whether the system calibration continues to be acceptable. As part of that process, it is determined whether the existing pressure-velocity relationship continues to be valid. If not, a recalibration can be initiated.

MULTIPLE PERTURBATIONS

For each of the different embodiments described hereto, an additional embodiment is described using multiple perturbation waveforms. All the features and advantages of the prior embodiments are applicable to these embodiments.

In the case of each of the previously described embodiments an embodiment is described in which the apparatus further induces a second exciter waveform into the arterial blood. An example second exciter waveform is one that has a frequency different from that of the first exciter waveform. It is noted that although the discussion of the second embodiment concentrates on a second exciter wave, any number of two or more exciter waves can be used to determine the perturbation velocity measurement.

In operation, processor 100 generates two exciter waveforms and communicates the waveforms to the exciter 202 via air tube 107. The exciter 202 responds by inducing both exciter waveforms into the patient. Noninvasive sensor 210 generates a signal responsive to a hemoparameter and transmits the signal to the processor 100 via wire 109.

The processor filters the noninvasive sensor signal into components of the natural waveform, a first exciter waveform, a second exciter waveform and noise. The processor determines the phase relationship of the first exciter waveform to a first reference input and determined the phase relationship of the second exciter waveform to a second reference input.

Once the processor has determined the phase of the exciter waveforms, the processor then generates a plurality of points, the slope of which relates to the velocity of the exciter waveform. This is shown in FIG. 8c, where the slope of the line is $-2\pi d/Vel$, and where d is distance and Vel is velocity. Since the distance is fixed and the slope is related to blood pressure, and since the slope changes based on changes in blood pressure, the velocity of the exciter waveform is determined.

The technique described above yields a measurement of the group velocity. In contrast, the techniques described in previous embodiments result in the measurement: of a phase velocity or of a pseudo-phase velocity in the case that the value of n of the phase equation (7) can not be uniquely determined. In a dispersive system these values need not always agree. However, phase, group and pseudo-velocity are monotonically varying functions of pressure. Thus, a measurement of any one of the three is a basis for a pressure prediction, so long as the appropriate pressure-velocity relationship is used.

An additional benefit of the use of multiple frequency perturbations is that it allows the unique determination of the value of n in the phase measurement equation described above. This allows the use of actual phase velocity, rather than of the pseudo-velocity described earlier in the multi-perturbation analogues of the embodiments depicted in FIGS. 6, 9 and 10.

Once the velocity is determined, a prediction of blood pressure is made according to FIG. 8a, showing the relationship of velocity to pressure. Thus, it is possible to determine the blood pressure with few, or zero, calibrations.

Figure 11:
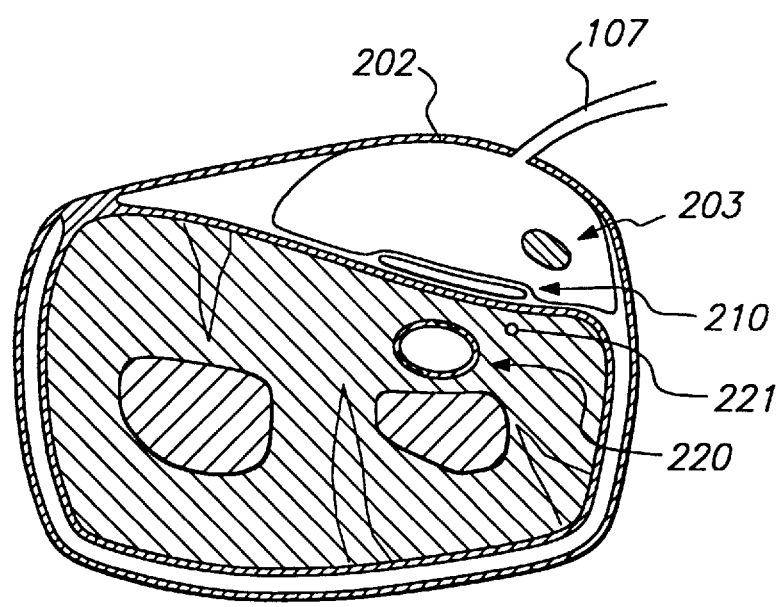

Another embodiment is depicted in FIG. 11 showing a cross section of an exciter 202 and noninvasive sensor 210 at the same position above the blood vessel 220. The proximate location of the exciter and the sensor permits measurement of the blood vessel's response to the perturbations. In this embodiment, the noninvasive sensor is responsive to a hemoparameter such as blood flow or blood volume. These parameters can be measured with a sensor such as a photoplethysmograph. Detected changes in the blood vessel due to the natural pulsatile pressure are calibrated using external exciter pressure oscillations and compared against the sensor signal by the processor.

VARIATIONS ON THE DISCLOSED EMBODIMENTS

Additional embodiments include an embodiment in which two or more detectors are positioned along the artery at different distances from a single exciter, and an embodiment in which two or more exciters are positioned along the artery at different. distances from one or more detectors. In each of these embodiments, the information. obtained from each exciter detector pair can be analyzed independently. The multiply redundant measurements of pressure that result can be combined to provide a single pressure determination that may be both more accurate and more immune from noise, motion artifact and other potential error sources. Similar redundancy can be achieved in the embodiments that use multiple exciter waveforms by analyzing the results at each frequency independently and combining the results to provide enhanced robustness.

In addition, any combination of more than two elements (e.g. two exciters and one detector, two detectors and one exciter, one exciter and three detectors) allows the value of n in the phase equation (7) to be uniquely determined so long as the spacing of two of the elements is sufficiently small to be less than a wavelength of the propagating perturbation. Since the possible range of perturbation wavelengths at a given-pressure can be determined from a pool of patients, selection of the appropriate spacing is straightforward and can be incorporated into the geometrical design of the device.

CONCLUSION

A close relationship between physiological parameters and hemoparameters supplies valuable information used in the present invention. The perturbation of body tissue and sensing the perturbation also supplies valuable information used in the present invention. Although the preferred embodiment concentrates on blood pressure, the present invention can also be used to analyze and track other physiological parameters such as vascular wall compliance, changes in the strength of ventricular contractions, changes in vascular resistance, changes in fluid volume, changes in cardiac output, myocardial contractility and other related parameters.

Calibration signals for the present invention can be obtained from a variety of sources including a catheter, manual determination, or other similar method.

The DC offset for the physiological parameter waveform can be obtained in a variety of ways for use with the present invention.

The exciter of the preferred embodiment uses air, but any suitable fluid can be used. Moreover, various exciter techniques can be used for inducing an exciter waveform into the patient such as an acoustic exciter, an electromagnetic exciter and an electromechanical exciter (e.g. piezoelectric device).

Various noninvasive sensors have been developed for sensing hemoparameters. These sensor types include piezoelectric, piezoresistive, impedance plethysmograph, photoplethysmograph, various types of strain gages, air cuffs, tonometry, conductivity, resistivity and other devices. The present invention can use any sensor that provides a waveform related to the hemoparameter of interest.

Having disclosed exemplary embodiments and the best mode, modifications and variations may be made to the disclosed embodiments while remaining within the subject and spirit of the invention as defined by the following claims.

What is claimed is:

1. A monitor for determining a physiological parameter of a patient comprising:

a calibration device configured to provide a calibration signal representative of one of the patient's physiological parameters;

an exciter adapted to be positioned over a blood vessel of the patient and configured to induce a transmitted exciter waveform into the patient;

a noninvasive sensor adapted to be positioned over said blood vessel and configured to sense a hemoparameter and to generate a noninvasive sensor signal representative of said hemoparameter containing a component of a received exciter waveform;

a processor configured to determine a relationship between a property of said received exciter waveform and a property of said physiological parameter;

wherein said processor includes a filter configured to separate a signal exciter waveform component of said noninvasive sensor signal from at least one other component of said noninvasive sensor signal; and wherein said processor is connected to receive said calibration signal and said noninvasive sensor signal and is configured to determine said physiological parameter based at least in part on said calibration signal, said signal exciter waveform component, and said relationship.

2. A monitor for determining a physiological parameter of a patient comprising:

a calibration device configured to provide a calibration signal representative of one of the patient's physiological parameters;

an exciter adapted to be positioned over a blood vessel of the patient and configured to induce a transmitted exciter waveform into the patient;

a noninvasive sensor adapted to be positioned over said blood vessel and configured to sense a hemoparameter and to generate a noninvasive sensor signal representative of said hemoparameter containing a component of a received exciter waveform;

a processor configured to determine a relationship between a property of said received exciter waveform and a property of said physiological parameter;

wherein said processor includes a filter configured to separate a component of said noninvasive sensor signal having a phase that varies with blood pressure from at least one other component of said noninvasive sensor signal having a phase that does not so vary; and wherein said processor is connected to receive said calibration signal and said noninvasive sensor signal and is configured to determine said physiological parameter based at least in part on said calibration signal, said component having a phase that varies with blood pressure, and said relationship.

3. The monitor of claim 2, wherein:
said processor includes a filter configured to determine an are representing time varying positions of said received exciter waveform, to determine a center point of said are and to determine a noise vector from an origin to said center point; and
said processor is configured to determine an arc vector from said center point to said time varying positions, where said arc vector has an arc vector angle that moves from a first angle to a second angle over time; and
wherein said processor is configured to process said arc vector angle to determine said physiological parameter.

4. The monitor of one of claims 1, 2 or 3, wherein:
said processor is further configured to determine a relationship between a component of said received exciter waveform and an amplitude and value of said physiological parameter.

5. The monitor of one of claims 1, 2 or 3, wherein:
said processor is further configured to determine a relationship between an amplitude and phase, of a component of said received exciter waveform and an amplitude and value of said physiological parameter.

6. A monitor for determining a physiological parameter of a patient, comprising:
a calibration device configured to provide a calibration signal representative of one of the patient's physiological parameters;
an exciter adapted to be positioned over a blood vessel of the patient and configured to induce a transmitted exciter waveform into the patient;
a noninvasive sensor adapted to be positioned over said blood vessel and configured to sense a hemoparameter and to generate a noninvasive sensor signal representative of said hemoparameter containing a component of a received exciter waveform;
a processor configured to determine a relationship between a property of said received exciter waveform and a property of said physiological parameter; and
wherein said processor is connected to receive said calibration signal and said noninvasive sensor signal and is configured to determine said physiological parameter based at least in part on said calibration signal, said noninvasive sensor signal and said relationship;
wherein said exciter is further configured to induce a second transmitted exciter waveform into the patient; and
wherein said processor includes a filter configured to separate from said noninvasive sensor signal a component of one of the group consisting of said physiological parameter waveform, said received exciter waveform, a second received exciter waveform, a signal exciter waveform, second signal exciter waveform and a noise waveform.

7. The monitor of one of claims 1, 2, 3 or 6, wherein:
said processor is responsive to said noninvasive sensor signal, and further configured to determine the validity of said calibration signal and to initiate a calibration when said calibration signal is not valid.

8. The monitor of one of claims 1, 2, 3 or 6, wherein:
said processor is further configured to scale said physiological parameter waveform based on the relationship between a property of said received exciter waveform and a property of said physiological parameter and to generate a scaled physiological parameter waveform signal.

9. A processor for determining a physiological parameter of a patient with an apparatus having a calibration device configured to provide a calibration signal representative of one of the patient's physiological parameters, an exciter adapted to be positioned over a blood vessel of the patient and configured to induce a transmitted exciter waveform into the patient, and a noninvasive sensor adapted to be positioned over said blood vessel and configured to sense a hemoparameter and to generate a noninvasive sensor signal representative of said hemoparameter, said processor comprising:
a first input configured to receive said calibration signal;
a second input configured to receive said noninvasive sensor signal;
a filter configured to from said noninvasive sensor signal a component representing a received exciter waveform;
a relationship routine configured to determine a relationship between a property of said received exciter waveform and a property of said physiological parameter;
wherein said filter is configured to separate a component of said noninvasive sensor signal having a phase that varies with blood pressure from at least one other component of said noninvasive sensor signal having a phase that does not so vary; and
a determination routine to determine said physiological parameter based at least in part on said calibration signal, said component having a phase that varies with blood pressure, and said relationship.

10. The processor of claim 9, wherein:
said filter is configured to determine an arc representing time varying positions of said received exciter waveform, to determine a center point of said arc and to determine a noise vector from an origin to said center point; and
said filter is configured to determine an arc vector from said center point to said time varying positions, where said arc vector has an arc vector angle that moves from a first angle to a second angle over time; and
wherein said determination routine is configured to process said are vector angle to determine said physiological parameter.

11. The processor of one of claims 9 or 10, wherein:
said determination routine is further configured to compare a phase relationship between said transmitted exciter waveform and a component of said noninvasive sensor signal to determine said physiological parameter.

12. The processor of one of claims 9 or 10 wherein:
said filter is further configured to separate from said noninvasive sensor signal a component representing a second received exciter waveform.

13. The processor of one of claims 9 or 10, wherein:
said determination routine is further configured to compare a phase relationship between said transmitted exciter waveform and a component of said noninvasive sensor signal, and to compare a phase relationship between a second transmitted exciter waveform and a component of said noninvasive sensor signal to determine said physiological parameter.

14. A method for determining a physiological parameter of a patient comprising:
providing a calibration signal representative of one of the patient's physiological parameters and storing the calibration signal;
inducing a transmitted exciter waveform into the patient;

noninvasively sensing a hemoparameter and generating a noninvasive sensor signal representative of said hemoparameter containing a component of a received exciter waveform; and processing said noninvasive sensor signal including the steps of:
(a) determining a relationship between a property of said received exciter waveform and a property of said physiological parameter;
(b) separating a signal exciter waveform component of said noninvasive sensor signal from at least one other component of said noninvasive sensor signal; and
(c) determining said physiological parameter based at least in part on said calibration signal, said signal exciter waveform component, and said relationship.

15. A method for determining a physiological parameter of a patient comprising:

providing a calibration signal representative of one of the patient's physiological parameters and storing the calibration signal;

inducing a transmitted exciter waveform into the patient;

noninvasively sensing a hemoparameter and generating a noninvasive sensor signal representative of said hemoparameter containing a component of a received exciter waveform; and processing said noninvasive sensor signal including the steps of:
(a) determining a relationship between a property of said received exciter waveform and a property of said physiological parameter;
(b) separating a signal exciter waveform a component of said noninvasive sensor signal having a phase that varies with blood pressure from at least one other component of said noninvasive sensor signal having a phase that does not so vary; and
(c) determining said physiological parameter based at least in part on said calibration signal, said component having a phase that varies with blood pressure, and said relationship.

16. The method of claim 15, wherein:

said processing step includes a filtering step of determining an arc representing time varying positions of said received exciter waveform, determining a center point of said arc and determining a noise vector from an origin to said center point; and said processing step includes a filtering step of determining an arc vector from said center point to said time varying positions, where said arc vector has an arc vector angle that moves from a first angle to a second angle over time.

17. The method of one of claims 14, 15 or 16, wherein:

said processing step includes determining a relationship between a component of said received exciter waveform and an amplitude and value of said physiological parameter.

18. The method of one of claims 14, 15 or 16, wherein:

said processing step includes determining a relationship between an amplitude and phase of a component of said received exciter waveform and an amplitude and value of said physiological parameter.

19. A of determining a physiological parameter of a patient, comprising the steps of:

providing a calibration signal representative of one of the patient's physiological parameters and storing the calibration signal;

inducing a transmitted exciter waveform into the patient;

noninvasively sensing a hemoparameter and generating a noninvasive sensor signal representative of said hemoparameter containing a component of a received exciter waveform;

processing said noninvasive sensor signal including the steps of:
(a) determining a relationship between a property of said received exciter waveform and a property of said physiological parameter; and
(b) determining said physiological parameter based at least in part on said calibration signal, said noninvasive sensor signal and said relationship;

inducing a second transmitted exciter waveform into the patient; and wherein said processing step includes a filtering step of separating from said noninvasive sensor signal a component of one of the group consisting of said physiological parameter waveform, said received exciter waveform, a second received exciter waveform, a signal exciter waveform, a second signal exciter waveform and a noise waveform.

20. The method of one of claims 14, 15, 16 or 19, wherein:

said processing step includes determining the validity of said calibration signal and initiating said step of providing a calibration signal when said calibration signal is not valid.

21. The method of one of claims 14, 15, 16 or 19, wherein:

said processing step includes scaling said physiological parameter waveform based on the relationship between a property of said received exciter waveform and a property of said physiological parameter and generating a scaled physiological parameter waveform signal.

22. A monitor for determining a patient's blood pressure comprising:

an inflatable cuff adapted to be positioned on an extremity of the patient and configured to provide a calibration signal representative of one of the patient's physiological parameters;

an exciter adapted to be positioned over a blood vessel of the patient and configured to induce a transmitted exciter waveform into the patient;

a noninvasive sensor adapted to be positioned over said blood vessel at a distance from said exciter and configured to sense a hemoparameter and to generate a noninvasive sensor signal representative of said hemoparameter containing a component of a received exciter waveform;

a processor configured to determine a relationship between a property of said received exciter waveform and a property of said physiological parameter;

wherein said processor is connected to receive said calibration signal and said noninvasive sensor signal;

wherein said processor includes a filter configured to separate a component of said noninvasive sensor signal having a phase that varies with blood pressure from at least one other component of said noninvasive sensor signal having a phase that does not so vary; and wherein said processor is configured to determine said blood pressure based at least in part on said calibration signal, said component having a phase that varies with blood pressure, and said relationship.

23. The monitor of claim 22, further comprising:

an exciter sensor adapted to be positioned near said exciter and configured to sense said transmitted exciter waveform and to generate an exciter sensor signal representative of said transmitted exciter waveform; and wherein said processor is further configured to compare the phase relationship of said transmitted exciter sensor signal and said received exciter waveform to determine said blood pressure.

24. A method of obtaining data of blood pressure of a patient, comprising:

noninvasively inducing into an artery of the patient a repetitive pressure wave;

noninvasively monitoring a characteristic of the repetitive wave upon modification by the artery;

determining a relationship between magnitudes of the monitored wave characteristic and blood pressure;

using the monitored wave characteristic and said relationship in a manner to provide the blood pressure of the patient; and noninvasively monitoring relative values of the blood pressure in the artery of the patient, and wherein using the monitored wave characteristic and said relationship includes scaling the monitored relative values of the blood pressure by the monitored wave characteristic and said relationship in a manner to provide absolute values of said blood pressure.

25. The method of claim 24, wherein monitoring the wave characteristic and monitoring the relative blood pressure values include use of a single transducer having an electrical signal output that is separated into components of the repetitive pressure wave and relative blood pressure by filtering.

26. A method of obtaining data of blood pressure of a patient, comprising:

noninvasively inducing into an artery of the patient a repetitive wave upon modification by the artery;

determining a relationship between magnitudes of the monitored wave characteristic and blood pressure;

using the monitored wave characteristic and said relationship in a manner to provide the blood pressure of the patient; and wherein using the monitored wave characteristic and said relationship includes processing the monitored characteristic of the pressure wave after modification by the artery in a manner to separate a component that varies with a period of the blood pressure from other, components that do not so vary, thereby to filter out a desired component of the monitored characteristic.

27. The method of claim 26, wherein the noninvasive monitoring of a characteristic of the repetitive wave includes measuring the characteristic between two spaced apart locations along a length of the artery.

28. The method of claim 27 wherein the characteristic being measured includes a relative phase of said pressure wave between said two spaced apart locations.

29. The method of one of claims 24, 25, 26 or 27, wherein determining the relationship between magnitudes of said wave characteristic and values of blood pressure is accomplished on the patient.

30. The method of one of claims 24, 25 and 27, wherein using the monitored wave characteristic and said relationship includes processing the monitored characteristic of the pressure wave after modification by the artery in a manner to separate a component that varies with a period of the blood pressure from other components that do not so vary, thereby to filter out a desired component of the monitored characteristic.

31. The method of one of claims 24, 25, 26, 27 or 28, which additionally comprises displaying the values of the blood pressure of the patient as a curve.

32. The method of one of claims 24, 25 or 26, wherein the noninvasive monitoring of a characteristic of the repetitive wave includes measuring the characteristic between two spaced apart locations along a length of the artery.

33. The method of one of claims 24, 25 or 26 wherein the noninvasive monitoring of a characteristic of the repetitive wave includes measuring the characteristic between two spaced apart locations along a length of the artery, and the characteristic being measured includes a relative phase of said pressure wave at said two spaced apart locations.

34. A method of obtaining data of blood pressure of a patient, comprising:

noninvasively inducing into an artery of the patient a repetitive pressure wave, noninvasively monitoring a characteristic of the pressure wave between two spaced apart locations along a length of the artery, processing the monitored characteristic of the pressure wave by separating a component that varies with a period of the blood pressure from other components that do not so vary, thereby to filter out a desired component of the monitored characteristic that is related to blood pressure, and determining the blood pressure from the filtered component.

35. The method of claim 34 wherein the monitored characteristic includes a relative phase of said pressure wave between said two spaced apart locations.

36. The method of claims 34 or 35, which additionally comprises displaying the determined blood pressure of the patient as a curve.

37. A monitor for determining a physiological parameter of a patient comprising:

an exciter adapted to be positioned over a blood vessel of the patient and configured to induce a transmitted exciter waveform into the patient;

a noninvasive sensor adapted to be positioned over said blood vessel and configured to sense a hemoparameter and to generate a noninvasive sensor signal representative of said hemoparameter containing a received exciter waveform component and a physiological waveform component;

a processor configured to utilize a relationship between a property of said received exciter waveform component and a property of said physiological parameter;

wherein said processor is configured to scale said noninvasive sensor signal including said physiological waveform component by use of said relationship to generate a scaled waveform; and wherein said processor is connected to receive said sensor signal and is configured to determine said physiological parameter based at least in part on said scaled waveform.

38. A monitor for determining a physiological parameter of a patient comprising:

an exciter adapted to be positioned over a blood vessel of the patient and configured to induce a transmitted exciter waveform into the patient;

a noninvasive sensor adapted to be positioned over said blood vessel and configured to sense a hemoparameter and to generate a noninvasive sensor signal representative of said hemoparameter containing a received exciter waveform component and a physiological waveform component;

a processor configured to utilize a relationship between a property of said received exciter waveform component and a property of said physiological parameter;

wherein said processor is connected to receive said sensor signal and is configured to determine said physiological parameter based at least in part on said sensor signal and said relationship; and means in addition to said sensor for noninvasively monitoring relative values of the physiological parameter of the patient, and wherein said processor is additionally configured for scaling the monitored relative values of the physiological parameter by the sensor signal and said relationship in a manner to provide absolute values of said physiological parameter.

39. A monitor for determining a physiological parameter of a patient comprising:

an exciter adapted to be positioned over a blood vessel of the patient and configured to induce transmitted exciter waveform into the patient;

a noninvasive sensor adapted to be positioned over said blood vessel and configured to sense a hemoparameter and to generate a noninvasive sensor signal representative of said hemoparameter containing a component of a received exciter waveform;

a processor configured to utilize a relationship between a property of said received exciter waveform and a property of said physiological parameter;

wherein said processor is connected to receive said sensor signal and is configured to determine said physiological parameter based at least in part on said sensor signal and said relationship; and wherein said processor is additionally configured for processing the sensor signal in a manner to separate a component that varies with a period of blood pressure variations in the artery from other components that do not so vary, thereby to filter out a desired component of the sensor signal.

40. The monitor according to claim 39, additionally comprising means coupled with said processor for displaying the values of the physiological parameter of the patient as a curve.

41. The monitor of one of claims 37, 38, 39 or 40 wherein the physiological parameter being monitored includes blood pressure.

42. A method for determining a physiological parameter of a patient comprising:

noninvasively positioning over a blood vessel of the patient an exciter that induces an exciter waveform into the blood vessel;

noninvasively positioning a sensor over the blood vessel of the patient at a location spaced a distance apart from the exciter along the blood vessel in order to detect a sensor signal of the exciter waveform at said spaced apart location that contains a component representative of a hemoparameter of the patient;

providing a relationship between a property of said sensor signal and a property of said physiological parameter;

separating a component of said noninvasive sensor signal having a phase that varies with blood pressure from at least one other component of said noninvasive sensor signal having a phase that does not so vary; and determining the physiological parameter from at least said component having a phase that varies with blood pressure, and said relationship.

43. The method of claim 42 wherein said step of determining the physiological parameter includes the step of measuring a phase of the sensor signal relative to that of the waveform induced into the blood vessel by the exciter.

44. The method of one of claims 42, or 43, wherein the physiological parameter of the patient being monitored includes blood pressure.

* * * * *

UNITED STATES PATENT AND TRADEMARK OFFICE
CERTIFICATE OF CORRECTION

PATENT NO. : 5,833,618
DATED : November 10, 1998
INVENTOR(S) : Caro et al.

It is certified that error appears in the above-identified patent and that said Letters Patent is hereby corrected as shown below:

Column 17, line 5, Claim 3, replace "are" with --arc--;
Column 17, line 21, Claim 5, replace "phase," with --phase--;
Column 18, line 40, Claim 10, replace "are" with --arc--;
Column 19, line 62, Claim 19, after first instance of "A", insert --method--;
Column 21, line 35, Claim 26, replace "wave upon modification by the artery" with --pressure wave--;
Column 21, between lines 35 and 36, Claim 26, insert the step --noninvasively monitoring a characteristic of the repetitive wave upon modification by the artery;--;

Signed and Sealed this

Eighteenth Day of January, 2000

Attest:

Q. TODD DICKINSON

*Attesting Officer*  *Commissioner of Patents and Trademarks*

UNITED STATES PATENT AND TRADEMARK OFFICE
CERTIFICATE OF CORRECTION

PATENT NO. : 5,833,618
DATED : November 10, 1998
INVENTOR(S) : Richard G. Caro et. al.

It is certified that error appears in the above-identified patent and that said Letters Patent is hereby corrected as shown below:

Column 16, line 38, Claim 1, delete "component,";
Column 16, line 66, Claim 2, replace "pressure," with --pressure--;
Column 18, line 15, Claim 9, after "to", insert --separate--;
Column 18, line 25, Claim 9, after "routine", insert --configured--;
Column 18, line 28, Claim 9, replace "pressure," with --pressure--;
Column 19, line 15, Claim 14, delete "component,";
Column 19, line 16, Claim 15, replace "for" with --of--;
Column 19, line 31, Claim 15, delete "a signal exciter waveform";
Column 19, line 38, Claim 15, replace "pressure," with --pressure--;
Column 20, line 62, Claim 22, replace "pressure," with --pressure--;
Column 24, line 10, Claim 42, replace "for determining " with --of monitoring--;
Column 24, line 27, Claim 42, after "parameter", insert --of the patient--; and
Column 24, line 29, Claim 42, replace "pressure," with --pressure--.

Signed and Sealed this

Fifteenth Day of May, 2001

Attest:

NICHOLAS P. GODICI

Attesting Officer

Acting Director of the United States Patent and Trademark Office